United States Patent
Edward

(10) Patent No.: US 10,386,281 B2
(45) Date of Patent: Aug. 20, 2019

(54) FLUID SENSOR

(71) Applicant: M-Flow Technologies Ltd., Abingdon (GB)

(72) Inventor: Giles Edward, Abingdon (GB)

(73) Assignee: M-Flow Technologies Ltd, Abingdon (GB)

( * ) Notice: Subject to any disclaimer, the term of this patent is extended or adjusted under 35 U.S.C. 154(b) by 478 days.

(21) Appl. No.: 14/437,600

(22) PCT Filed: Oct. 22, 2013

(86) PCT No.: PCT/GB2013/052755
§ 371 (c)(1),
(2) Date: Apr. 22, 2015

(87) PCT Pub. No.: WO2014/064436
PCT Pub. Date: May 1, 2014

(65) Prior Publication Data
US 2015/0300936 A1    Oct. 22, 2015

(30) Foreign Application Priority Data

Oct. 22, 2012 (GB) .................................. 1218956.9

(51) Int. Cl.
*G01R 27/00*  (2006.01)
*G01N 11/00*  (2006.01)
(Continued)

(52) U.S. Cl.
CPC ............. *G01N 11/00* (2013.01); *G01N 22/00* (2013.01); *G01N 27/00* (2013.01);
(Continued)

(58) Field of Classification Search
CPC .................... G01N 11/00; G01N 27/00; G01N 2011/0066; G01N 33/2847; G01N 22/00
See application file for complete search history.

(56) References Cited

U.S. PATENT DOCUMENTS 3,688,188 A    8/1972 Bak et al.
4,287,495 A *  9/1981 Lund, Jr. ............... H01P 3/122
                                                      138/130
(Continued)

FOREIGN PATENT DOCUMENTS

EP    0 564 879    10/1993
EP    8 889 321    1/1999
(Continued)

OTHER PUBLICATIONS

Espacenet English translation of WADA JP411118733A, Apr. 30, 1999.*
(Continued)

*Primary Examiner* — Melissa J Koval
*Assistant Examiner* — Courtney G McDonnough
(74) *Attorney, Agent, or Firm* — Levy & Grandinetti

(57) ABSTRACT

A fluid sensor (10) comprises a base member (20) defining a fluid flow path (21), a cavity filler member (26) located externally of the base member (20), and a cavity member (30) located externally of the base member (20) and the cavity filler member (26). The cavity member (30) is configured so as to provide confinement for an electromagnetic field. The base member (20) and the cavity filler member (26) are both configured so as to permit transmission of electromagnetic radiation at a frequency of the electromagnetic field therethrough. The electromagnetic field may be a radio frequency (RF) electromagnetic field. The base member (20) and/or the cavity member (30) may define an outer cavity region externally of the base member (20). The cavity filler member (26) may completely or partially fill the outer cavity region. The fluid sensor (10) may be used in the measurement of the composition and/or flow characteristics of a fluid in the fluid flow path (21).

40 Claims, 13 Drawing Sheets

(51) Int. Cl.
  *G01N 33/28* (2006.01)
  *G01N 27/00* (2006.01)
  *G01N 22/00* (2006.01)
  *G01N 22/04* (2006.01)

(52) U.S. Cl.
  CPC ......... *G01N 33/2847* (2013.01); *G01N 22/04* (2013.01); *G01N 2011/0066* (2013.01)

(56) References Cited

U.S. PATENT DOCUMENTS

| | | | | |
|---|---|---|---|---|
| 5,103,181 | A | * | 4/1992 | Gaisford ............ G01N 33/2823 324/637 |
| 7,610,816 | B2 | | 11/2009 | Okazaki |
| 2009/0107252 | A1 | * | 4/2009 | Okazaki ................ G01F 1/56 73/861.25 |
| 2012/0092008 | A1 | * | 4/2012 | Krioutchkov ........ G01N 24/081 324/307 |
| 2013/0255821 | A1 | * | 10/2013 | Roberts ................ B29C 70/202 138/177 |
| 2014/0182737 | A1 | * | 7/2014 | Jones ................... G01N 22/00 138/177 |

FOREIGN PATENT DOCUMENTS

| | | |
|---|---|---|
| EP | 1 584 920 | 10/2005 |
| EP | 1 855 104 | 11/2007 |
| EP | 1 895 290 | 3/2008 |
| FI | 834892 | 7/1985 |
| GB | 2271637 A | 4/1994 |
| GB | 2365978 A | 2/2002 |
| GB | 2468754 A | 9/2010 |
| JP | H10-332606 | 12/1998 |
| JP | H118733 A | 4/1999 |
| JP | H11118733 A * | 4/1999 ............. G01N 22/04 |
| WO | WO 2012/072993 | 6/2012 |
| WO | WO 2012/095631 | 7/2012 |
| WO | WO 2014/076506 | 5/2014 |
| WO | WO 2015/001323 | 1/2015 |

OTHER PUBLICATIONS

Search Report received in corresponding Great Britain Application No. GB1218956.9, dated Feb. 20, 2013.

International Search Report and Written Opinion received in corresponding application No. PCT/GB2013/052755, dated Apr. 23, 2014.

Boyachok, John H. et al., "Analysis of a Microwave Void Fraction Meter," IEEE Transactions on Industrial Electronics and Control Instrumentation, vol. 1(1), pp. 34-43 (Feb. 1, 1975).

Rzepecka, Maria A. et al., "High Frequency Monitoring of Residual and Bound Water in Nonconductive Fluids," IEEE Transactions on Instrumentation and Measurement, vol. 1(3), pp. 205-209 (Sep. 1975).

Hauschild, Thorsten, "Density and Moisture Measurements Using Microwave Resonators," Electromagnetic Aquametry, pp. 193-215 (Jan. 1, 2005).

Al-Hajeri, S. et al., "An electromagnetic cavity sensor for multiphase measurement in the oil and gas industry," Journal of Physics: Conference Series, vol. 76(1) (Jul. 1, 2007).

Al-Hajeri, S. et al., "Real time EM waves monitoring system for oil industry three phase flow measurement," Journal of Physics: Conference Series, vol. 178(1) (Jul. 1, 2009).

Scussiato, Eduardo et al., "Desenvolvimento de um medidor de fracao de agua para esoamento bifasico (agua e oleo) utilizando tecnicas de micro-ondas em cavidade ressonante," 5th Congresso Brasileiro de Pesquisa e Desenvolvimento em Petroleo e Gas (Oct. 2009).

\* cited by examiner

FLUID SENSOR

FIELD

The present invention relates to a fluid sensor for measuring a composition and/or flow characteristics of a fluid and, in particular, though not exclusively for measuring the oil, gas and/or water content and flow rate of a fluid in a pipe and/or in an oil or gas well.

BACKGROUND

It is known to use fluid sensors to measure the composition and/or flow characteristics of a fluid. Such fluid sensors are often referred to as multiphase meters. Known multiphase meters comprise a base pipe defining a fluid flow path internally thereof surrounded by a concentrically arranged open-ended generally cylindrical metallic cavity member. The base pipe is substantially transparent to radio frequency (RF) electromagnetic radiation. The cavity member defines a resonant cavity for a RF electromagnetic field which extends through the base pipe and across the fluid flow path. In known multiphase meters the base pipe may be formed of polyvinyl chloride (PVC) or polyether ether ketone (PEEK) and the cavity member is formed of brass. Such known multiphase meters are configured to detect a resonant peak in the frequency spectrum of the RF electromagnetic field and to extract the composition and/or flow characteristics of fluid in the fluid flow path from characteristics of the resonant peak.

It is well known that the strength of an RF electromagnetic field varies across a resonant cavity. Consequently, when a non-homogeneous fluid is present in the fluid flow path, different fluid components (e.g. water, oil or gas) present in the fluid may be located or flow through regions having significantly different RF electromagnetic field strengths. If the different fluid components move position across the fluid flow path this can make measurements of the composition and/or flow characteristics of the fluid in the fluid flow path more difficult and/or less accurate. Accordingly, in known multiphase meters, the cavity member is generally separated from the base pipe so as to define a resonant cavity which is significantly greater in cross-section than the fluid flow path for improved uniformity of the RF electromagnetic field strength across the fluid flow path. Consequently, known multiphase meters have an annular outer cavity region defined between an outer surface of the base pipe and an inner surface of the cavity member.

In known multiphase meters the annular outer cavity region is filled with air or water. Examples of such known multiphase meters are described in S. Al-Hajeri, S. R. Wylie, R. A. Stuart and A. I. Al-Shamma'a, "An electromagnetic cavity sensor for multiphase measurement in: the oil and gas industry", Journal of Physics: Conference Series 76 (2007) 012007; in S. Al-Hajeri, S. R. Wylie, A. Shaw and A. I. Al-Shamma'a "Real time EM waves monitoring system for oil industry three phase flow measurement", Journal of Physics: Conference Series 178 (2009) 012030; in S. R. Wylie, A. I. Al-Shamma'a, A. Shaw and S. Al-Hajeri, "Electromagnetic cavity sensors for multiphase measurement", Exploration and Production Oil and Gas Review, Volume 9, Issue 1; and in Finnish patent document no. FI834892.

The use of a fluid sensor comprising an air-filled outer cavity region may be problematic especially in a high pressure environment because it may be necessary for the cavity member to be configured to withstand high external pressures. Similarly, if the cavity member is surrounded by a casing for protection in a high pressure environment, it may be necessary for the casing to be configured to withstand high external pressures. In a subsea environment, it may also be important to provide the air-filled outer cavity region with high pressure seals to prevent water ingress. Moreover, for high internal fluid pressures within the fluid flow path it may be necessary for the base pipe to be configured to withstand the high internal fluid pressures for similar reasons.

The use of a fluid sensor comprising a water-filled outer cavity region may also be problematic because water has a relatively high conductivity. This may result in absorption of the RF electromagnetic field in the water-filled outer cavity region and may make it difficult to detect a resonant peak in the RF electromagnetic field. This may make measurements of the composition and/or flow characteristics of the fluid in the fluid flow path more difficult and/or less accurate. Moreover, although water is generally much less compressible than air, if the external and/or internal fluid pressures are sufficiently high, it may still be necessary for the cavity member and/or the base pipe to be configured to withstand high external and/or high internal fluid pressures. To prevent any reduction in structural integrity of the fluid sensor, it may also be important to provide the water-filled outer cavity region with high pressure seals to prevent water egress.

In addition, for the case of known fluid sensors having air- or water-filled outer cavity regions where the base pipe comprises a polymeric material, pressurised fluids, particularly gasses, can migrate from the fluid flow path through the polymeric material over time and accumulate in the outer cavity region. This can be problematic if the fluid sensor is later subjected to a reduction in internal or external fluid pressure because such depressurisation may lead to expansion of the accumulated fluids and may result in deformation or, in the worst case, structural failure of the fluid sensor.

SUMMARY

According to a first aspect of the present invention there is provided a fluid sensor comprising:

a base member defining a fluid flow path;

a cavity filler member located externally of the base member; and a cavity member located externally of the base member and the cavity filler member, wherein the cavity member is configured so as to provide confinement for an electromagnetic field, and the base member and the cavity filler member are each configured so as to permit transmission therethrough of electromagnetic radiation at a frequency of the electromagnetic field.

The electromagnetic field may comprise a radio frequency (RF) electromagnetic field, a microwave field, a mm-wave field, an optical field or an electromagnetic field of any other frequency.

The electromagnetic field may have a frequency in the range, 1 kHZ to 1 THz, 10 kHz to 100 GHz, 100 kHz to 10 GHz, or 1 MHz to 1 GHz.

The base member, the cavity filler member and the cavity member may each comprise one or more solid materials.

The base member, the cavity filler member and the cavity member may be separately formed.

The base member and/or the cavity member may define an outer cavity region externally of the base member.

The cavity filler member may completely fill the outer cavity region. Compared with known fluid sensors having an air- or water-filled outer cavity region, this may permit the fluid sensor to withstand higher external and/or internal fluid pressures. Alternatively, for a given external and/or internal fluid pressure, this may permit a weaker or thinner-walled cavity member and/or a weaker or thinner-walled base member to be used. Moreover, if the cavity filler member completely fills the outer cavity region so that there are no voids, spaces or gaps within the outer cavity region, this may serve to prevent migration of any pressurised fluid and, in particular, any pressurised gases from the external environment through the cavity member into the outer cavity region or from the fluid flow path through the base member into the outer cavity region. This may prevent or at least mitigate the accumulation of pressurised fluid within the outer cavity region and any potential problems associated with deformation or structural collapse of the fluid sensor on depressurisation. This may also avoid any requirement for high pressure seals, or at least reduce the required sealing performance, to prevent water ingress into an air-filled outer cavity region when the fluid sensor is located in a subsea environment or to prevent water egress from a water-filled outer cavity region. Compared with known fluid sensors having a water-filled outer cavity region, this may also reduce absorption of the RF electromagnetic field thereby simplifying and/or improving the accuracy of measurements of the composition, distribution and/or flow characteristics of the fluid in the fluid flow path.

The cavity filler member may partially fill the outer cavity region. Compared with known fluid sensors having an outer cavity region which has the same volume but which is air- or water-filled, this may serve to reduce the volume of air or water present in the outer cavity region. Compared with known fluid sensors having an outer cavity region which has the same volume but which is air- or water-filled, this may permit the fluid sensor to withstand higher external and/or internal fluid pressures. Alternatively, for a given external and/or internal fluid pressure, this may permit a weaker or thinner-walled cavity member and/or a weaker or thinner-walled base member to be used. Moreover, even if the cavity filler member only partially fills the outer cavity region, the resulting voids, spaces or gaps within the outer cavity region will be smaller than the outer cavity region itself. This may serve to reduce migration of any pressurised fluid and, in particular, any pressurised gases from the external environment through the cavity member into the outer cavity region or from the internal fluid flow path through the base member into the outer cavity region. This may avoid or at least mitigate any potential problems associated with the deformation or structural collapse of the fluid sensor on depressurisation. Compared with known fluid sensors having an outer cavity region which has the same volume but which is water-filled, this may also reduce absorption of the RF electromagnetic field thereby simplifying and/or improving the accuracy of measurements of the composition, distribution and/or flow characteristics of the fluid in the fluid flow path. The location of the cavity member externally to the base member may avoid any compromise in the strength or integrity of the base member that may otherwise result if the cavity member were embedded within the base member.

The base member may be substantially transparent to transmission of electromagnetic radiation at the frequency of the electromagnetic field. Such a base member may permit electromagnetic radiation at a frequency of the electromagnetic field to penetrate therethrough without unduly absorbing energy. The base member may be substantially electrically non-conductive at a frequency of the electromagnetic field.

The base member may comprise a dielectric material.

The base member may comprise a material having a permittivity which is relatively constant over a lifetime of the fluid sensor. This may make simplify and/or enhance the accuracy of the determination of the composition, distribution and/or flow characteristics of a fluid over the lifetime of the fluid sensor.

The base member may comprise a material having a permittivity which is relatively insensitive to temperature. This may make simplify and/or enhance the accuracy of the determination of the composition, distribution and/or flow characteristics of a fluid over a wider range of temperatures.

The base member may comprise a material having a permittivity which is relatively insensitive to the permeation of fluids such as air or water into or through the base member. This may make simplify and/or enhance the accuracy of the determination of the composition, distribution and/or flow characteristics of a fluid even if fluids such as air or water into or through the base member migrate through or partially penetrate the base member.

The base member may comprise a material having a permittivity which changes in a predictable quantifiable manner as a function of time over a lifetime of the fluid sensor.

The base member may comprise a material having a permittivity which changes in a predictable quantifiable manner as a function of temperature.

The base member may comprise a material having a permittivity which changes in a predictable quantifiable manner as a function of the degree of permeation of fluids such as air or water into or through the base member.

The base member may be a structural member.

The base member may be a strength member.

The base member may be configured to withstand a predetermined pressure or a predetermined force exerted on an interior of the base member such as a predetermined pressure or a predetermined force exerted as a result of fluid pressure in the fluid flow path.

The base member may be configured to withstand a predetermined pressure and/or force.

The base member may be configured to withstand a predetermined axial tension, a predetermined axial compression and/or a predetermined bending stress.

The base member may be configured to withstand a predetermined pressure and/or force exerted on an exterior of the base member such as an external fluid pressure exerted on an exterior of the base member.

The base member may be configured to withstand external pressures that may exist subsea or external pressures that may exist in an oil or gas well.

The base member may comprise a polymer material.

The base member may comprise a thermoplastic material.

The base member may comprise a thermoset material.

The base member may comprise a polyaryl ether ketone, a polyaryl ketone, a polyether ketone (PEK), a polyether ether ketone (PEEK), a polycarbonate and/or the like.

The base member may comprise polyvinyl chloride (PVC).

The base member may comprise a polyamide.

The base member may comprise polyamide 11 (PA11).

The base member may comprise polyvinylidene fluoride, or polyvinylidene difluoride (PVDF).

The base member may comprise polyphenylene sulphide (PPS).

The base member may comprise polyethylenimines (PEI).

The base member may comprise polyoxymethylene (POM) or acetal.

The base member may comprise a resin such as a setting resin, a polymeric resin, an epoxy resin or the like.

The base member may be formed from a composite material comprising a matrix and one or more reinforcing elements embedded within the matrix.

The matrix of the base member may be substantially transparent to transmission of electromagnetic radiation at a frequency of the electromagnetic field.

The matrix of the base member may be substantially electrically non-conductive at a frequency of the electromagnetic field.

The matrix of the base member may comprise a polymer material.

The matrix of the base member may comprise a thermoplastic material.

The matrix of the base member may comprise a thermoset material.

The matrix of the base member may comprise a polyaryl ether ketone, a polyaryl ketone, a polyether ketone (PEK), a polyether ether ketone (PEEK), a polycarbonate and/or the like.

The matrix of the base member may comprise polyvinyl chloride (PVC).

The matrix of the base member may comprise a polyamide.

The matrix of the base member may comprise polyamide 11 (PA11).

The matrix of the base member may comprise polyvinylidene fluoride, or polyvinylidene difluoride (PVDF).

The matrix of the base member may comprise polyphenylene sulphide (PPS).

The matrix of the base member may comprise polyethylenimines (PEI).

The matrix of the base member may comprise polyoxymethylene (POM) or acetal.

The matrix of the base member may comprise a resin such as a setting resin, a polymeric resin, an epoxy resin or the like.

The one or more reinforcing elements of the base member may be substantially transparent to transmission of electromagnetic radiation at a frequency of the electromagnetic field.

The one or more reinforcing elements of the base member may be substantially electrically non-conductive at a frequency of the electromagnetic field.

The one or more reinforcing elements of the base member may comprise continuous or elongate elements.

The one or more reinforcing elements of the base member may comprise fibres, strands, filaments, nanotubes or the like.

The one or more reinforcing elements of the base member may comprise discontinuous elements.

The one or more reinforcing elements of the base member may comprise polymeric fibres, for example aramid fibres.

The one or more reinforcing elements of the base member may comprise non-polymeric fibres, for example, glass, basalt fibres and/or the like.

The one or more reinforcing elements of the base member may comprise E-glass.

The matrix and the reinforcing elements of the base member may comprise similar or identical materials. For example, the reinforcing elements of the base member may comprise the same material as the matrix of the base member, albeit in a fibrous, drawn, elongate form or the like.

The base member may define the fluid flow path internally thereof.

The base member may be tubular.

The base member may comprise a fluid conduit such as a pipe or the like.

The base member may comprise a portion of a pipeline.

The base member may comprise a chemically inert material. Such a base member may be relatively immune to or withstand the flow of corrosive substances therethrough thus preserving the structural integrity of the base member. Such a base member may, for example, be relatively immune to corrosion from hydrogen sulphide, carbon dioxide, acids formed by the reaction of these gases with water and/or any other corrosive substances produced from a hydrocarbon bearing formation. Such a base member may also be relatively immune to or withstand the flow of chemicals which are typically injected into oil or gas wells during an intervention procedure to enhance production from a hydrocarbon bearing formation.

The cavity filler member may be substantially transparent to electromagnetic radiation at the frequency of the electromagnetic field.

The cavity filler member may comprise at least one of the materials of which the base member may comprise.

The cavity filler member may comprise a hard solid material.

The cavity filler member may comprise a soft solid material.

The cavity filler member may comprise a resilient solid material.

The cavity filler member may comprise an expandable or a swellable solid material. For example, the cavity filler member may be configured to expand or swell on contact with a fluid. For example, the cavity filler member may be configured to expand or swell on contact with any fluid that may penetrate or migrate through the base member and/or the cavity member. Such a cavity filler member may provide additional support to the base member and/or the cavity member in the event that fluid penetrates or migrates through the base member and/or the cavity member.

The cavity filler member may provide structural support to the base member.

The cavity filler member may extend between the base member and the cavity member.

The cavity filler member may extend from an outer surface of the base member to an inner surface of the cavity member.

The cavity filler member may be generally tubular.

The cavity filler member may have an outer shape, profile and/or dimension which varies along a direction of the fluid flow path.

The cavity filler member may have an outer radial dimension which varies along a direction of the fluid flow path.

The cavity filler member may have an outer diameter which varies along a direction of the fluid flow path.

The cavity filler member may have at least one rounded or tapered end.

The cavity filler member may be homogeneous.

The cavity filler member may be non-homogeneous.

The cavity filler member may be formed and then fitted relative to the base member. Once formed, the cavity filler member may be fitted over, on and/or around the base member. Once formed, the cavity filler member may be cold-fitted over, on and/or around the base member.

The cavity filler member may be formed in situ relative to the base member.

The cavity filler member may be formed in situ over, on and/or around the base member.

The cavity filler member may be formed by a casting, moulding, machining and/or deposition process.

The cavity filler member may be integrally or monolithically formed.

The cavity filler member may comprise multiple component parts.

The cavity filler member may be laminated.

The component parts may be separately formed and subsequently assembled to form the cavity filler member.

Formation of an integrally or monolithically formed cavity filler member may induce a temperature gradient across the cavity filler member. Depending on the composition and/or dimensions of the integrally or monolithically formed cavity filler member, the temperature gradient may result in internal stresses within the cavity filler member. Such internal stresses may compromise the structural integrity of an integrally or monolithically formed cavity filler member. Such internal stresses may lead to the formation of discontinuities, fissures, cracks, voids and/or the like in the cavity filler member. This may in turn reduce the transparency of an integrally or monolithically formed cavity filler member to electromagnetic radiation at the frequency of the electromagnetic field. Furthermore, pressurised or corrosive fluids may migrate into the discontinuities, fissures, cracks, voids and/or the like in the cavity filler member. This may compromise the structural integrity of the cavity filler member and/or the fluid sensor, for example on reduction or depressurisation of external and/or internal fluid pressure. In addition, the formation of discontinuities, fissures, cracks, voids and/or the like in integrally or monolithically formed cavity filler members may result in a degradation in the quality and/or production yield of such cavity filler members resulting in higher production costs. Separately forming multiple component parts and subsequently assembling the component parts together to form the cavity filler member may serve to avoid the formation of discontinuities, fissures, cracks, voids and/or the like in the cavity filler member, may serve to preserve the structural integrity of the cavity filler member and/or may serve to eliminate or at least partially mitigate any reduction in the transparency associated with an integrally or monolithically formed cavity filler member.

The component parts of the cavity filler member may be assembled together to form the cavity filler member before fitting the cavity filler member relative to the base member.

The component parts of the cavity filler member may be assembled together relative to the base member so as to form the cavity filler member in situ relative to the base member. The component parts of the cavity filler member may be assembled over, on and/or around the base member so as to form the cavity filler member in situ relative to the base member.

The cavity filler member may comprise multiple sleeves, for example multiple tubular sleeves. The cavity filler member may comprise a first sleeve which is configured to be fitted concentrically relative to the base member. For example, the first sleeve may be assembled over, on and/or around the base member. The cavity filler member may comprise one or more subsequent sleeves. Each subsequent sleeve may be configured to be fitted concentrically relative to a previous sleeve until the cavity filler member is complete. For example, each subsequent sleeve may be assembled over, on and/or around a previous sleeve until the cavity filler member is complete.

Each component part of the cavity filler member may be generally flat. A generally flat component part may be formed more readily than a tubular sleeve. A generally flat component part may be machined from a sheet, for example cut, punched and/or stamped from a sheet.

Each generally flat component part may have a pair of generally parallel opposing faces.

Each generally flat component part may comprise an aperture formed therein.

Each generally flat component part may have a generally circular outer edge.

Each generally flat component part may be generally annular.

Each generally flat component part may have a non-circular outer edge.

The base member may extend through the aperture of each generally flat component part.

The cavity filler member may be formed by arranging each generally flat component part sequentially over, on and/or around the base member. The generally flat component parts may be arranged so that respective faces of adjacent generally flat component parts engage one another.

Each generally flat component part may have an aperture formed therein which is arranged concentrically with respect to an outer circumference of the generally flat component part.

Each generally flat component part may have an aperture formed therein which is arranged eccentrically with respect to an outer circumference of the generally flat component part. Such generally flat component parts may be used for the construction of a cavity filler member which is arranged eccentrically with respect to the base member. Such an eccentric arrangement may, in use, provide a different electromagnetic field distribution across the fluid flow path. This may be advantageous for detecting the composition, distribution and/or flow characteristics of a fluid component which is only travelling through a localised area of a cross-section of the fluid flow path.

The component parts of the cavity filler member may be formed with predetermined dimensional tolerances so as to eliminate or minimise any gaps therebetween. In this way, the dimensions of any gaps between adjacent component parts of the cavity filler member may be controlled so as to minimise any associated reduction in the transparency of the cavity filler member.

The component parts of the cavity filler member may be may be bonded, adhered, fused, welded or otherwise joined together. The component parts of the cavity filler member may be bonded together using a bonding agent such as an adhesive, an epoxy or the like. The bonding agent may be transparent to electromagnetic radiation at the frequency of the electromagnetic field.

The cavity filler member may be bonded, adhered, fused, welded or otherwise joined to the base member.

The cavity member may completely confine the electromagnetic field.

The cavity member may only partially confine the electromagnetic field. For example, a portion of the electromagnetic field may extend beyond an outer envelope of the cavity member.

The cavity member may comprise an electrically conductive material

The cavity member may comprise a metal.

The cavity member may comprise at least one of copper, brass, gold, silver, aluminium, iron, steel, and the like.

The cavity member may comprise an electrically conductive composite material comprising a matrix and one or more reinforcing elements embedded within the matrix.

The one or more reinforcing may be electrically-conductive.

The matrix of the cavity member may be electrically-conductive.

The matrix of the cavity member may comprise a polymer material.

The matrix of the cavity member may comprise a thermoplastic material.

The matrix of the cavity member may comprise a thermoset material.

The matrix of the cavity member may comprise a polyaryl ether ketone, a polyaryl ketone, a polyether ketone (PEK), a polyether ether ketone (PEEK), a polycarbonate and/or the like.

The matrix of the cavity member may comprise polyvinyl chloride (PVC).

The matrix of the cavity member may comprise a polyamide.

The matrix of the cavity member may comprise polyamide 11 (PA11).

The matrix of the cavity member may comprise polyvinylidene fluoride, or polyvinylidene difluoride (PVDF).

The matrix of the cavity member may comprise polyphenylene sulphide (PPS).

The matrix of the cavity member may comprise polyethylenimines (PEI).

The matrix of the cavity member may comprise polyoxymethylene (POM) or acetal.

The matrix of the cavity member may comprise a resin such as a setting resin, a polymeric resin, an epoxy resin or the like.

The one or more reinforcing elements of the cavity member may be substantially opaque to transmission of electromagnetic radiation at a frequency of the electromagnetic field.

The one or more reinforcing elements of the cavity member may comprise continuous or elongate elements.

The one or more reinforcing elements of the cavity member may comprise fibres, strands, filaments, nanotubes or the like.

The one or more reinforcing elements of the cavity member may comprise discontinuous elements.

The one or more reinforcing elements of the cavity member may comprise particles, clusters, pieces and/or the like.

The one or more reinforcing elements of the cavity member may comprise carbon.

The Applicant has discovered that the use of a cavity member comprising a composite material including a PEEK matrix and carbon fibre reinforcing elements embedded within the PEEK matrix is surprisingly effective for providing confinement for a RF electromagnetic field and, in particular, for an electromagnetic field having a frequency in the approximate range 1 MHz to 100 GHz. It is thought that a cavity member comprising an electrically-conductive composite material may be capable of providing confinement of an electromagnetic field having a frequency in the range, 1 kHZ to 1 THz, 10 kHz to 100 GHz, 100 kHz to 10 GHz, or 1 MHz to 1 GHz. An electrically conductive composite cavity member may not only provide confinement for a RF electromagnetic field, but may also be sufficiently strong to withstand external fluid pressures in a subsea environment or in the environment of an oil or gas well. Moreover, an electrically conductive composite cavity member may be relatively resistant to erosion and/or corrosion compared with known brass cavity members. The use of an electrically conductive composite cavity member may avoid any requirement for the use of a thick brass cavity member to withstand external fluid pressures. The use of an electrically conductive composite cavity member may also avoid any requirement for a separate external casing such as a steel external casing for the protection of a known brass cavity member. In addition, an electrically conductive composite cavity member may be more easily formed, fitted and/or applied over the core compared with known brass cavity members. An electrically conductive composite cavity member may be more easily integrated as part of a composite pipeline.

The one or more reinforcing elements of the cavity member may be metallic. The one or more reinforcing elements may comprise metal fibres, metal particles, metal clusters, metal pieces and/or the like.

The cavity member may comprise reinforcing elements comprising at least one of copper, brass, gold, silver, aluminium, iron, steel, and the like.

The cavity member may be formed remotely from the cavity filler member.

The cavity member may be fitted relative to the cavity filler member. The cavity member may be fitted over, on and/or around the cavity filler member. The cavity member may be cold-fitted relative to the cavity filler member.

The cavity member may be formed in situ relative to the cavity filler member. For example, the cavity member may be formed by manipulating, working, bending, wrapping, machining, coating, dipping, depositing or otherwise applying cavity member material over, on and/or around the cavity filler member.

The cavity member may be formed in situ relative to the cavity filler member by forming a layer such as a foil or a sheet of material over, on and/or around the cavity filler member.

The cavity member may be generally cylindrical.

The cavity member may have an aperture formed therein. A portion of the electromagnetic field may, in use, extend through the aperture.

The cavity member may have two opposite ends, each end having an aperture formed therein.

The cavity member may comprise a generally tubular main body portion.

The generally tubular main body portion may be electrically conductive.

The cavity member may comprise a generally planar end portion.

The generally planar end portion may be electrically conductive.

The end portion may have an aperture formed therein.

The end portion may be generally annular.

The main body portion and the end portion may be integrally formed.

The main body portion and the end portion may be separately formed.

The main body portion and the end portion may be electrically connected.

The end portion may engage the main body portion. For example, a face of the end portion may abut an annular end face of the main body portion.

The cavity member may comprise a generally tubular main body portion and a generally planar end portion at each end thereof, wherein each of the end portions has an aperture formed therein and a respective face of each of the end portions engages a respective end face of the main body portion. Such a cavity member configuration may at least partially accommodate a core which extends through the apertures of the end portions, whilst also providing confinement of the electromagnetic field especially in vicinity of the apertures of the end portions.

The main body portion and the end portion of the cavity member may be bonded, adhered, fused, welded or otherwise joined together.

The main body portion and the end portion of the cavity member may comprise the same material.

The main body portion and the end portion of the cavity member may comprise different materials. For example, the main body portion of the cavity member may be formed from the electrically-conductive composite material and the end portion of the cavity member may be formed from a metal.

The cavity member may have an open end.

The cavity member may have an open end and a closed end.

The cavity member may be separated from an outer surface of the core.

The cavity member may engage the outer surface of the core.

The cavity member may have an inner diameter greater than an outer diameter of the core.

The cavity member may comprise a main body portion and an end portion extending from the main body portion. The main body portion may be generally cylindrical. The main body portion may have an inner diameter which is greater than an outer diameter of the core. The end portion may be generally tubular. The end portion may have a reduced inner diameter relative to the inner diameter of the main body portion. The end portion may have an inner diameter which is substantially equal to an outer diameter of the core. Such a cavity member may serve to confine the electromagnetic field in the vicinity of the end portion more effectively than a generally cylindrical cavity member having a generally planar end portion.

The cavity member may comprise generally tubular end portions, each end portion extending from a different end of the main body portion. Each tubular end portion may have a reduced inner diameter relative to the inner diameter of the main body portion. Such a cavity member may serve to confine the electromagnetic field in the vicinity of the end portions more effectively than a generally cylindrical cavity member having planar end portions. Each tubular end portion may have an inner diameter which is substantially equal to an outer diameter of the core.

The cavity member may be concentrically aligned with respect to the base member.

The cavity member may be eccentrically aligned with respect to the base member. Such an eccentric arrangement of the cavity member relative to the base member may provide a different electromagnetic field distribution across the fluid flow path. This may be advantageous for detecting the composition and/or flow characteristics of a fluid component which is only travelling through a localised area of a cross-section of the fluid flow path.

The cavity member axis may be oriented radially relative to the base member axis. Such a radially oriented cavity member may comprise an aperture formed in an end thereof which is disposed towards the base member. The electromagnetic field may extend from the aperture through a wall of the base member and into the fluid flow path. Such a radially oriented cavity member may comprise an open end which is disposed towards the base member. The electromagnetic field may extend from the open end of the cavity member through a wall of the base member and into the fluid flow path.

The cavity member may be bonded, adhered, fused, welded or otherwise joined to the base member and/or to the cavity filler member.

The fluid sensor may comprise an arrangement for creating the electromagnetic field.

The fluid sensor may comprise an antenna for coupling an electromagnetic signal to and/or from the electromagnetic field.

The fluid sensor may comprise a plurality of antennas, each antenna configured to couple a corresponding electromagnetic signal to and/or from the electromagnetic field.

The fluid sensor may comprise a first antenna which couples a corresponding electromagnetic signal to the electromagnetic field and a second antenna which couples a corresponding electromagnetic signal from the electromagnetic field.

The antenna may extend through the cavity member.

The antenna may be electrically insulated from cavity member. This may permit the electromagnetic field to extend between the antenna and the cavity member.

The antenna may be located externally of the base member. This avoids any compromise in the strength or integrity of the base member that may otherwise result if the antenna were to extend into the base member.

The antenna may extend partially through the cavity filler member.

The antenna may be embedded within the cavity filler member.

The antenna may be located externally to the fluid flow path, at, adjacent or near to an inner surface of the base member.

The antenna may be located, for example embedded within the base member. Such an arrangement may only be possible where the base member is sufficiently strong to accommodate the antenna and/or any associated cabling, and/or where the base member is supported by surrounding structures such as the cavity filler member so as to provide sufficient strength to accommodate the antenna and/or any associated cabling. Such an arrangement may allow the antenna to be located close or adjacent to the fluid flow path without extending into the fluid flow path. This may permit a measurement of a composition, distribution and/or flow rate of any fluid present in the fluid flow path whilst also avoiding any potential damage to the antenna that may otherwise occur if the antenna extended into the fluid flow path due to corrosion and/or erosion, for example due to the composition and/or the flow of fluid, debris, particulates or the like in the fluid flow path. This may also reduce the possibility of obstruction of the fluid flow path due to snagging or build up of debris, particulates or the like on or around the antenna that might otherwise occur if the antenna extended into the fluid flow path. This may also permit pigging of the fluid flow path if required.

The antenna may extend partially through the base member.

The antenna may be embedded within the base member.

The antenna may extend through the base member into the fluid flow path. This may, for example, be necessary to permit electromagnetic energy to be transmitted to and/or from any fluid present in the fluid flow path without transmission of the electromagnetic energy through the base member. This may eliminate or at least reduce energy loss from and/or distortion of the electromagnetic field in the base member.

The fluid sensor may comprise a source of electromagnetic energy for creation of the electromagnetic field.

The electromagnetic energy source may be coupled to the one or more antennas. The one or more antennas may transmit electromagnetic energy from the electromagnetic energy source to any fluid present in the fluid flow path via the electromagnetic field.

The fluid sensor may be configured so as to prevent amplification by the electromagnetic energy source of any electromagnetic energy which is coupled from the electromagnetic field back through the electromagnetic energy source. The frequency of the electromagnetic field created by such a fluid sensor may be independent of the configuration of the core, the configuration of the cavity member and of any fluid present in the fluid flow path. Such a fluid sensor may permit electromagnetic energy to be provided to any fluid present in the fluid flow path. Energy may be provided to a fluid present in the fluid flow path for the purposes of determining at least one of a composition, distribution and/or flow rate of the fluid. Energy may be provided to a fluid present in the fluid flow path for the purposes of heating the fluid, agitating the fluid, exciting the fluid and/or imaging the fluid.

The fluid sensor may be configured for amplification of electromagnetic energy which is coupled from the electromagnetic field back through the electromagnetic energy source. The electromagnetic energy source may be configured to amplify electromagnetic energy which is coupled from the electromagnetic field back through the electromagnetic energy source. The one or more antennas, the cavity member and the electromagnetic field may provide a feedback path for the electromagnetic energy created in the electromagnetic energy source. The one or more antennas, the cavity member, the electromagnetic field and the electromagnetic energy source may together define a resonant system.

The electromagnetic energy source may provide sufficient amplification of the electromagnetic energy circulating in the resonant system to overcome any losses experienced by the electromagnetic energy circulating in the resonant system, thereby creating the electromagnetic field. Such a fluid sensor may create an electromagnetic field having a complex frequency spectrum comprising an amplitude frequency spectrum and a phase frequency spectrum, wherein each of the amplitude and phase frequency spectra of the complex frequency spectrum are dependent on the configuration of the resonant system and, in particular on the configuration of the core, the configuration of the cavity member and on any fluid present in the fluid flow path. Each of the amplitude and phase frequency spectra of the complex frequency spectrum may include one or more resonance features. Each resonance feature may have a frequency, size and/or shape which vary according to the configuration of the core, the configuration of the cavity member and on any fluid present in the fluid flow path. Each resonance feature may have a frequency, size and/or shape which vary according to the composition, distribution and/or flow characteristics of any fluid in the fluid flow path.

The electromagnetic energy source may comprise at least one of a gain medium, an amplifier, and a negative resistance.

The electromagnetic energy source may comprise an oscillator.

The oscillator may be configured to oscillate at a predetermined frequency at or around a frequency of one or more of the resonance features in the amplitude and/or phase frequency spectra of the complex frequency spectrum of the electromagnetic field.

The oscillator may be configured to sweep a frequency of the electromagnetic energy across a frequency range which includes a frequency of one or more of the resonance features in the amplitude and/or phase frequency spectra of the complex frequency spectrum of the electromagnetic field.

The fluid sensor may be configured to tap the electromagnetic field.

The fluid sensor may be configured to provide an output electromagnetic signal which is proportional to or representative of a strength of the electromagnetic field.

The fluid sensor may be configured to provide an output electromagnetic signal which is proportional to or representative of an electromagnetic signal coupled to and/or from the electromagnetic field by the one or more antennas and/or by the cavity member.

The electromagnetic energy source may be located externally to the cavity member.

The electromagnetic energy source may be located adjacent to the cavity member.

The electromagnetic energy source may be located adjacent to the antenna.

The fluid sensor may comprise an electrical enclosure.

The electromagnetic energy source may be located within the electrical enclosure.

The electrical enclosure may be sufficiently strong to withstand external forces and/or external fluid pressures in a subsea environment or in the environment of an oil or gas well.

The electrical enclosure may be configured to be resistant to erosion and/or corrosion.

The electrical enclosure may be configured to prevent fluid ingress into an interior of the electrical enclosure.

The electrical enclosure may be attached to the cavity member.

The electrical enclosure may be attached to an outer surface of the cavity member.

The fluid sensor may comprise a bracket and/or one or more fasteners which attach the electrical enclosure to the cavity member.

The electrical enclosure may be partially located, accommodated and/or embedded within the cavity member.

The electrical enclosure may be wholly located, accommodated and/or embedded within the cavity member. Wholly locating, accommodating and/or embedding the electrical enclosure within the cavity member may serve to protect the interior of the electrical enclosure and the oscillator from external forces, external pressure, erosion and/or corrosion.

The electrical enclosure may be located between inner and outer layers of the cavity member. The fluid sensor may comprise a temperature sensor for sensing a temperature of a fluid in the fluid flow path.

The temperature sensor may comprise a resistance temperature detector (RTD), a thermocouple, a thermistor, a thermometer or the like.

The temperature sensor may be configured to withstand temperatures in excess of the temperatures involved in the formation of any material within which the temperature sensor is embedded.

The temperature sensor may be configured to withstand temperatures of greater than 400° C. that may occur during the casting of any PEEK material within which the temperature sensor is embedded.

The temperature sensor may comprise a platinum resistance thermometer. A platinum resistance thermometer may be particularly suitable as a temperature sensor because a platinum resistance thermometer is accurate and may withstand temperatures of greater than 400° C.

The temperature sensor may be located externally of the base member.

The temperature sensor may be located externally to the base member, at, adjacent or near to an outer surface of the base member. Such an arrangement of the temperature sensor avoids any compromise to the integrity of the base member that would otherwise occur if the temperature sensor were located within the base member or if the temperature sensor and/or any associated cabling extended through the base member.

The temperature sensor may be located, for example embedded within the base member. Such an arrangement may allow the temperature sensor to be located close to the fluid flow path for the measurement of a temperature which is close to or at least representative of a temperature of any fluid present in the fluid flow path. Such an arrangement may only be possible where the base member is sufficiently strong to accommodate the temperature sensor and/or any associated cabling, and/or where the base member is supported by surrounding structures such as the cavity filler member so as to provide sufficient strength to accommodate the temperature sensor and/or any associated cabling.

Such an arrangement may allow the temperature sensor to be located close or adjacent to the fluid flow path without extending into the fluid flow path. This may permit a measurement of a temperature which is close to or at least representative of a temperature of any fluid present in the fluid flow path whilst also avoiding any potential damage to the temperature sensor that may otherwise occur if the temperature sensor extended into the fluid flow path from corrosion and/or erosion, for example due to the composition and/or the flow of fluid, debris, particulates or the like in the fluid flow path. This may also reduce the possibility of obstruction of the fluid flow path due to snagging or build up of debris, particulates or the like on or around the temperature sensor that might otherwise occur if the temperature sensor extended into the fluid flow path. This may also permit pigging of the fluid flow path if required.

The temperature sensor may extend through the base member into the fluid flow path. This may, for example, be necessary for the accurate measurement of temperature of any fluid present in the fluid flow path.

The temperature sensor may be located externally to the cavity member. Such an arrangement would avoid any disruption or distortion of the electromagnetic field that would otherwise occur if the temperature sensor were located within the cavity member.

The fluid sensor may comprise an external casing configured to protect the cavity member.

The external casing may be configured to withstand external pressure such as external fluid pressure. For example, the external casing may be configured to withstand external pressures that may exist subsea and/or external pressures that may exist in an oil or gas well.

The external casing may comprise a metal such as steel, aluminium or the like.

The external casing may comprise a composite material comprising a matrix and one or more reinforcing elements embedded within the matrix.

The matrix of the external casing may comprise a polymer material.

The matrix of the external casing may comprise a thermoplastic material.

The matrix of the external casing may comprise a thermoset material.

The matrix of the external casing may comprise may comprise polyvinyl chloride (PVC).

The matrix of the external casing may comprise a polyamide.

The matrix of the external casing may comprise polyamide 11 (PA11).

The matrix of the external casing may comprise polyvinylidene fluoride, or polyvinylidene difluoride (PVDF).

The matrix of the external casing may comprise polyphenylene sulphide (PPS).

The matrix of the external casing may comprise polyethylenimines (PEI).

The matrix of the external casing may comprise polyoxymethylene (POM) or acetal.

The matrix of the external casing may comprise a polyaryl ether ketone, a polyaryl ketone, a polyether ketone (PEK), a polyether ether ketone (PEEK), a polycarbonate and/or the like.

The matrix of the external casing may comprise a polymeric resin, such as an epoxy resin or the like.

The one or more reinforcing elements of the external casing may comprise continuous or elongate elements.

The one or more reinforcing elements of the external casing may comprise fibres, strands, filaments, nanotubes or the like.

The one or more reinforcing elements of the external casing may comprise discontinuous elements.

The one or more reinforcing elements of the external casing may comprise polymeric fibres, for example aramid fibres.

The one or more reinforcing elements of the external casing may comprise non-polymeric fibres, for example, carbon, glass, basalt fibres and/or the like.

The one or more reinforcing elements of the external casing may comprise E-glass.

The matrix and the reinforcing elements of the external casing may comprise similar or identical materials. For example, the reinforcing elements of the external casing may comprise the same material as the matrix of the external casing, albeit in a fibrous, drawn, elongate form or the like.

The fluid sensor may define an extra-cavity region externally of the cavity member and internally of the external casing.

The extra-cavity region may be at least partially filled with a filler material.

The filler material may comprise a potting compound such as a solid or gelatinous potting compound. Such a filler material may serve to provide the fluid sensor with a degree of resistance to shock and vibration. Such a filler material may serve to prevent the penetration of fluid from the external environment into the extra-cavity region. Such a filler material may serve to prevent the ingress of a corrosive agent from the external environment into the extra-cavity region.

The filler material may comprise a thermo-setting plastic or a silicone rubber material such as a silicone rubber gel or the like.

The filler material may comprise an incompressible material. Such a filler material may serve to support the external casing against external pressure.

The filler material may comprise neoprene or the like.

The fluid sensor may comprise a flange configured to permit connection of the fluid sensor to an adjacent fluid conduit or an adjacent fluid sensor.

The fluid sensor may comprise a flange at either end.

The flange may comprise at least one of the materials of which the external casing may comprise.

The flange may be sealed relative to the base member.

The fluid sensor may comprise an inner seal member for sealing the flange relative to the base member.

The flange may be configured to accommodate the base member and/or the inner seal member.

The inner seal member may be configured to provide a seal between a surface of the flange and a surface such as an end face of the base member.

The inner seal member may be generally annular.

The inner seal member may be configured to be adjacent to and/or exposed to the fluid flow path. Such an inner seal member may prevent the escape of fluid from the fluid flow path along an interface between the base member and the flange.

The inner seal member may comprise a resilient material.

The inner seal member may accommodate the temperature sensor and/or any associated cabling. For example, the temperature sensor and/or any associated cabling may be embedded within the inner seal member or inserted into a passageway formed within the inner seal member.

The inner seal member may comprise a thermally conductive material. The use of an inner seal member comprising thermally conductive material may permit any temperature sensor accommodated within the inner seal member to sense a temperature which is as close as possible or at least representative of a temperature of a fluid in the fluid flow path.

The inner seal member may comprise at least one of the materials of which the external casing may comprise.

For example, the inner seal member may comprise a PEEK matrix and one or more carbon fibre reinforcing elements embedded within the PEEK matrix. The incorporation of one or more carbon fibres into the inner seal member may enhance not only the strength but also the thermal conductivity of the inner seal member.

The fluid sensor may comprise an outer seal member for sealing the flange relative to the external casing.

The flange may be configured to accommodate the external casing and/or the outer seal member.

The outer seal member may be configured to provide a seal between a surface of the flange and a surface such as an end face of the external casing.

The outer seal member may be generally annular.

The outer seal member may comprise an O-ring.

The outer seal member may be configured to be adjacent to and/or exposed to an environment external to the fluid sensor. Such an outer seal member may prevent the ingress of fluid from the external environment along an interface between the external casing and the flange.

The outer seal member may comprise a resilient material.

The outer seal member may comprise an elastomeric material.

The fluid sensor may comprise one or more tie bars extending from one flange to the other.

Each tie bar may comprise a metal such as steel, aluminium or the like.

Each tie bar may comprise a composite material comprising a matrix and one or more reinforcing elements embedded within the matrix.

Each tie bar may be attached at either end to a flange. The tie bars may be configured to provide structural support for the fluid sensor. For example, the tie bars may be configured to withstand tension, compression and/or bending stresses applied to the fluid sensor.

The flanges and/or the tie bars may be configured to compress an inner seal member between a flange and the base member during assembly of the fluid sensor so as to form a seal between the flange and the base member.

The flanges and/or the tie bars may be configured to compress an outer seal member between a flange and the external casing during assembly of the fluid sensor so as to form a seal between the flange and the external casing.

The fluid sensor may comprise a demodulator.

The demodulator may be configured to demodulate an electromagnetic signal at or around a frequency of the electromagnetic field.

The demodulator may be configured to receive the output electromagnetic signal.

The demodulator may be configured to demodulate the output electromagnetic signal to a lower frequency electromagnetic signal.

The demodulator may be located externally to the cavity member.

The demodulator may be located adjacent to the cavity member.

The demodulator may be located adjacent to the antenna.

The demodulator may be located within the electrical enclosure.

The demodulator may be located remotely from the cavity member.

The demodulator may be located remotely from the antenna.

The demodulator may be coupled to at least one of the cavity member, the antenna and the electromagnetic energy source by an electrical conductor, a waveguide, a cable and/or the like.

The fluid sensor may comprise a processor.

The processor may be configured to receive a demodulated electromagnetic signal which is demodulated from the output electromagnetic signal.

The processor may be configured to receive the demodulated signal from the demodulator.

The processor may be configured to determine the amplitude and/or phase frequency spectrum of the electromagnetic field from the demodulated signal.

The processor may be configured to determine the composition, distribution and/or flow characteristics of any fluid in the fluid flow path from the determined amplitude and/or phase frequency spectrum of the electromagnetic field.

The processor may be configured to determine the frequency, size and/or shape of a resonance feature in the amplitude and/or phase frequency spectrum of the electromagnetic field from the demodulated signal.

The processor may be configured to determine the composition, distribution and/or flow characteristics of any fluid in the fluid flow path from the frequency, size and/or shape of a resonance feature in the frequency spectrum of the electromagnetic field.

The processor may be configured to receive temperature information from the thermocouple.

The processor may be configured to use the received temperature information to determine the composition, distribution and/or flow characteristics of the fluid in the fluid flow path from the determined amplitude and/or phase frequency spectrum of the electromagnetic field.

The processor may be located externally to the cavity member.

The processor may be located adjacent to the cavity member.

The processor may be located within the electrical enclosure.

The processor may be located remotely from the cavity member.

The processor may be located remotely from the antenna.

The processor may be located remotely from the demodulator.

The processor may be coupled to the demodulator by an electrical conductor, a waveguide, a cable and/or the like.

The fluid sensor may comprise a memory.

The memory may store calibration data which relates the amplitude and/or phase frequency spectrum of the electromagnetic field to known compositions, distributions and/or flow rates of fluid in the fluid flow path.

The memory may store calibration data which relates the amplitude and/or phase frequency spectrum of a demodulated signal to known compositions, distributions and/or flow rates of fluid in the fluid flow path.

The memory may store calibration data which relates a frequency, size and/or shape of a resonance feature in the amplitude and/or phase frequency spectrum of the electromagnetic field to known compositions, distributions and/or flow rates of fluid in the fluid flow path.

The processor may be configured to receive the calibration data from the memory.

The processor may be configured to use the calibration data and the determined amplitude and/or phase frequency spectrum of the electromagnetic field to determine the composition, distribution and/or flow rate of any fluid in the fluid flow path.

The processor may be configured to use the calibration data and the determined frequency, size and/or shape of a resonance feature in the amplitude and/or phase frequency spectrum of the electromagnetic field to determine the composition, distribution and/or flow rate of any fluid in the fluid flow path.

The fluid sensor may comprise a plurality of cavity members, wherein each cavity member extends along a corresponding axis which is arranged radially relative to the base member axis, and the cavity members are distributed circumferentially relative to the base member axis.

The fluid sensor may comprise a plurality of cavity members distributed axially along the base member axis.

Two or more of the cavity members may be configured so as to at least partially define a respective cavity for producing electromagnetic fields having the same resonant frequency or for producing electromagnetic fields having different resonant frequencies.

According to a second aspect of the present invention there is provided a method for use in manufacturing a fluid sensor, the method comprising:

providing a base member defining a fluid flow path;

locating a cavity filler member externally of the base member;

locating a cavity member externally of the base member and the cavity filler member, wherein the cavity member is configured so as to provide confinement for an electromagnetic field, and the base member and the cavity filler member are each configured so as to permit transmission therethrough of electromagnetic radiation at a frequency of the electromagnetic field.

The method may comprise separately forming the base member, the cavity filler member and the cavity member.

The method may comprise forming the cavity filler member remotely from the base member.

The method may comprise fitting the cavity filler member relative to the base member.

The method may comprise fitting the cavity filler member over, on and/or around the base member. The method may comprise cold-fitting the cavity filler member over, on and/or around the base member.

The method may comprise forming the cavity filler member in situ relative to the base member.

The method may comprise forming the cavity filler member in situ over, on and/or around the base member.

The method may comprise forming the cavity filler member by a casting, moulding, machining and/or deposition process.

The method may comprise integrally or monolithically forming the cavity filler member.

The method may comprise assembling the cavity filler member from multiple component parts.

The method may comprise assembling the component parts of the cavity filler member to form the cavity filler member before fitting the cavity filler member relative to the base member.

The method may comprise assembling the component parts of the cavity filler member together relative to the base member so as to form the cavity filler member in situ relative to the base member. The method may comprise assembling the component parts of the cavity filler member over, on and/or around the base member so as to form the cavity filler member in situ relative to the base member.

The method may comprise assembling the cavity filler member from multiple sleeves, for example multiple tubular sleeves.

The method may comprise arranging the sleeves concentrically relative to the base member.

The method may comprise fitting a first sleeve concentrically relative to the base member.

The method may comprise fitting a subsequent sleeve concentrically relative to the first sleeve.

The method may comprise concentrically fitting one or more further sleeves, one over the other until the cavity filler member is complete.

The method may comprise assembling the cavity filler member from multiple generally flat component parts.

Each generally flat component part may have a pair of generally parallel opposing faces.

Each generally flat component part may comprise an aperture formed therein.

Each generally flat component part may have a generally circular outer edge.

Each generally flat component part may be generally annular.

Each generally flat component part may have a non-circular outer edge.

The method may comprise extending the base member through the aperture of each generally flat component part.

The method may comprise arranging each generally flat component part sequentially over, on and/or around the base member.

The method may comprise arranging the generally flat component parts so that respective faces of adjacent generally flat component parts engage one another.

Each generally flat component part may have an aperture formed therein which is arranged concentrically with respect to an outer circumference of the generally flat component part.

Each generally flat component part may have an aperture formed therein which is arranged eccentrically with respect to an outer circumference of the generally flat component part. The method may comprise bonding, adhering, fusing, welding or otherwise joining the component parts of the cavity filler member together.

The method may comprise bonding the component parts of the cavity filler member together using a bonding agent such as an adhesive, an epoxy or the like. The bonding agent may be transparent to electromagnetic radiation at the frequency of the electromagnetic field.

The method may comprise bonding, adhering, fusing, welding or otherwise joining the cavity filler member to the base member.

It should be understood that one or more of the optional features associated with the first aspect may apply alone or in any combination in relation to the second aspect.

According to a third aspect of the present invention there is provided a fluid sensor system comprising a plurality of fluid sensors, each fluid sensor comprising:

a base member defining a fluid flow path;

a cavity member located externally of the base member and configured so as to provide confinement for an electromagnetic field; and a cavity filler member located externally of the base member and internally of the cavity member, wherein the base member and the cavity filler member are each configured so as to permit transmission therethrough of electromagnetic radiation at a frequency of the electromagnetic field.

The plurality of fluid sensors may be coupled, joined, connected, welded, bonded or otherwise attached in an end-to-end relation.

The plurality of fluid sensors may together define a fluid sensor system flow path which comprises the fluid flow path of each of the individual fluid sensors.

Two or more of the fluid sensors may be configured to create respective electromagnetic fields at the same resonant frequency or to create respective electromagnetic fields having different resonant frequencies.

It should be understood that one or more of the optional features associated with the first or second aspects may apply alone or in any combination in relation to the third aspect.

BRIEF DESCRIPTION OF THE DRAWINGS

The present invention will now be described by way of non-limiting example only with reference to the following figures of which.

DETAILED DESCRIPTION OF THE DRAWINGS

Figure 1:
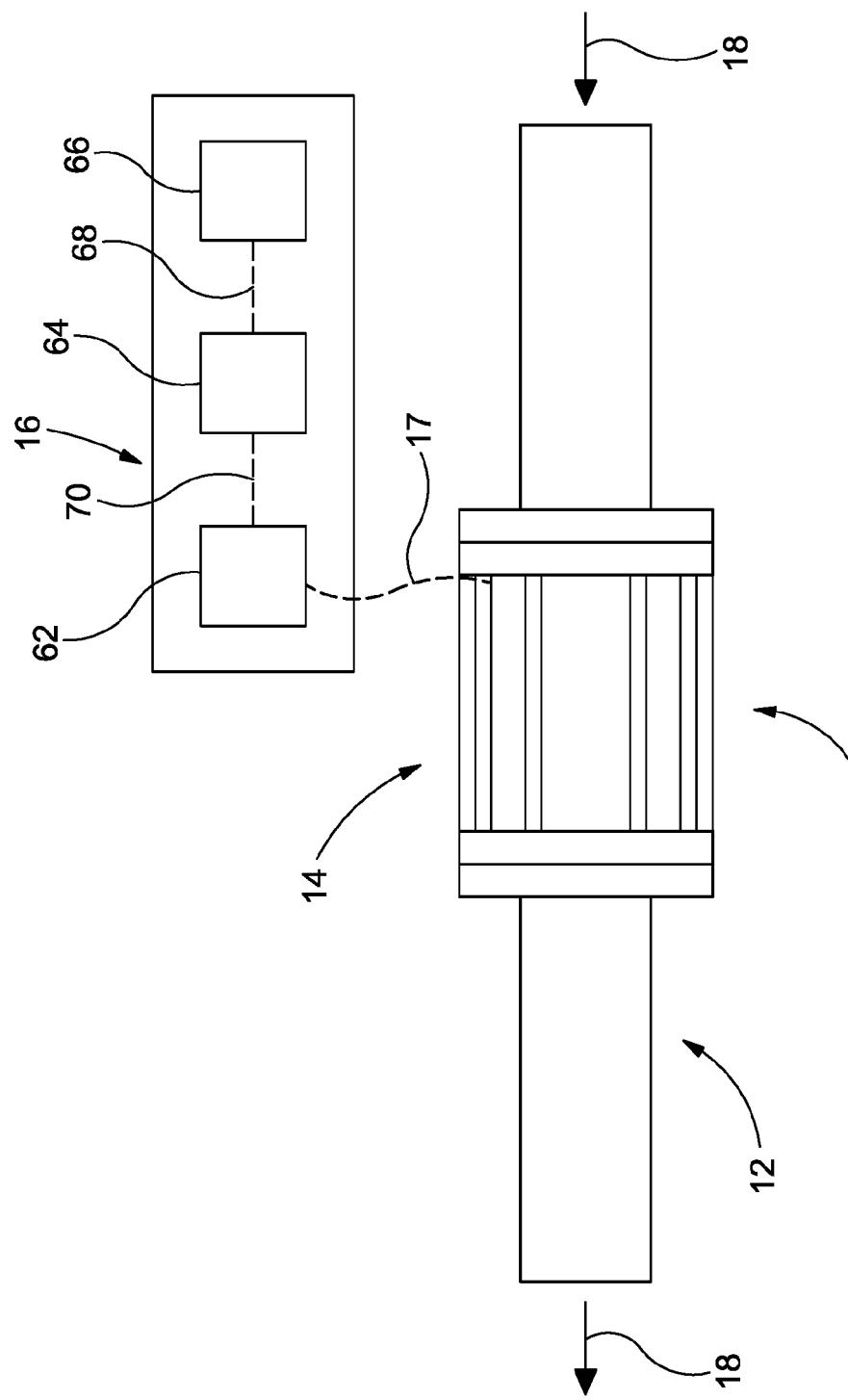
FIG. 1 is a schematic of a fluid sensor connected into a pipeline for measuring a composition and/or flow characteristics of a fluid in the pipeline.

Referring initially to FIG. 1, there is shown a fluid sensor generally designated 10 for measuring a composition, distribution and/or flow characteristics of a fluid flowing in a pipeline 12. The fluid sensor comprises a main body portion generally designated 14 which is connected into and forms part of the pipeline 12 so that a continuous fluid flow path extends along the pipeline 12 through the main body portion 14 of the fluid sensor 10. The fluid sensor 10 comprises electronic instrumentation 16. As indicated by the dotted line 17, the main body portion 14 of the fluid sensor 10 and the electronic instrumentation 16 are configured for communication with one another. In use, as indicated by the arrows 18, fluid flows along the pipeline 12 through the main body portion 14 of the fluid sensor 10. The electronic instrumentation 16 receives a signal from the main body portion 14 of the fluid sensor 10 and determines the composition and/or flow characteristics of the fluid flowing along the pipeline 12 from the received signal. It should be understood that the pipeline 12 may be located above ground. Alternatively, the pipeline 12 may form part of a subterranean and/or subsea oil or gas well. For example, the pipeline 12 may comprise production tubing or a drill string or the like. The pipeline 12 may comprise a casing of a subterranean and/or a subsea oil or gas well. The pipeline 12 may comprise a riser such as a marine riser or the like which is configured to extend from a subsea wellhead of a subsea oil or gas well to a surface vessel or a surface platform.

Figure 2:
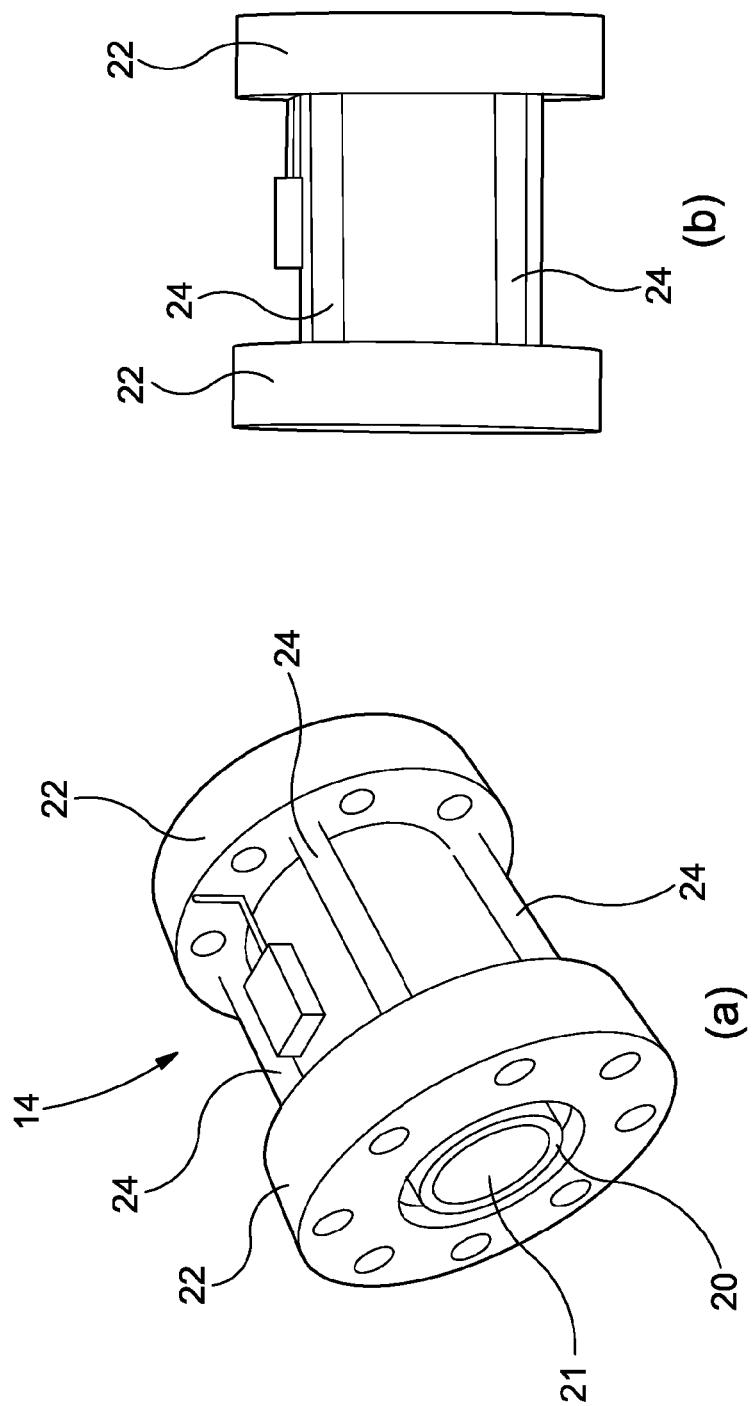
FIG. 2(a) shows a main body portion of the fluid sensor of FIG. 1 after removal of an external casing and filler material.
FIG. 2(b) is a side view of FIG. 2(a)
Figure 3:
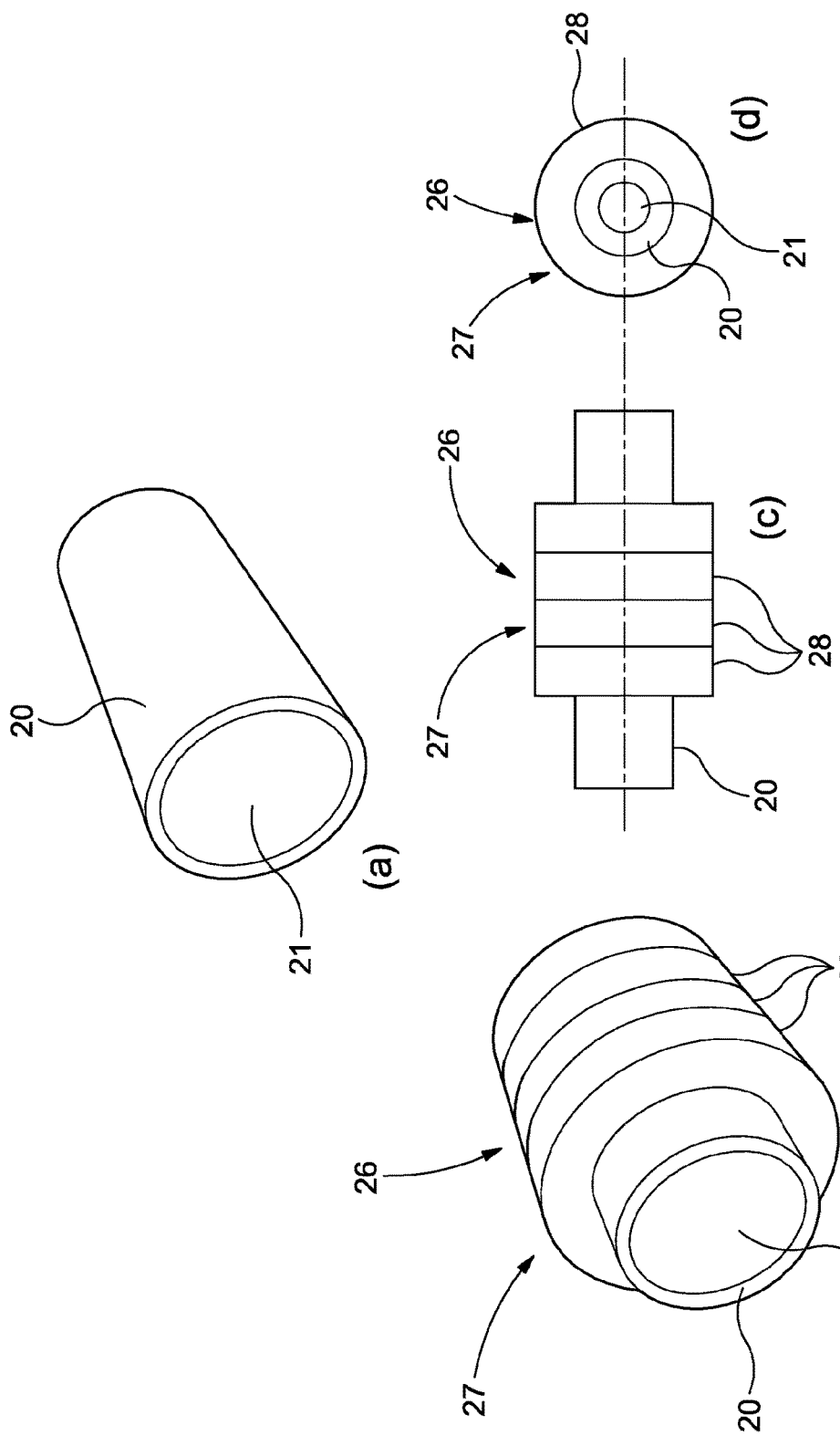
FIG. 3(a) shows a base pipe of the fluid sensor of FIG. 1.
FIG. 3(b) shows a core comprising the base pipe of FIG. 3(a) and a cavity filler member formed from multiple rings mounted on the base pipe.
FIG. 3(c) is a side view of the core of FIG. 3(b)
FIG. 3(d) is an end view of the core of FIG. 3(b)
Figure 4:
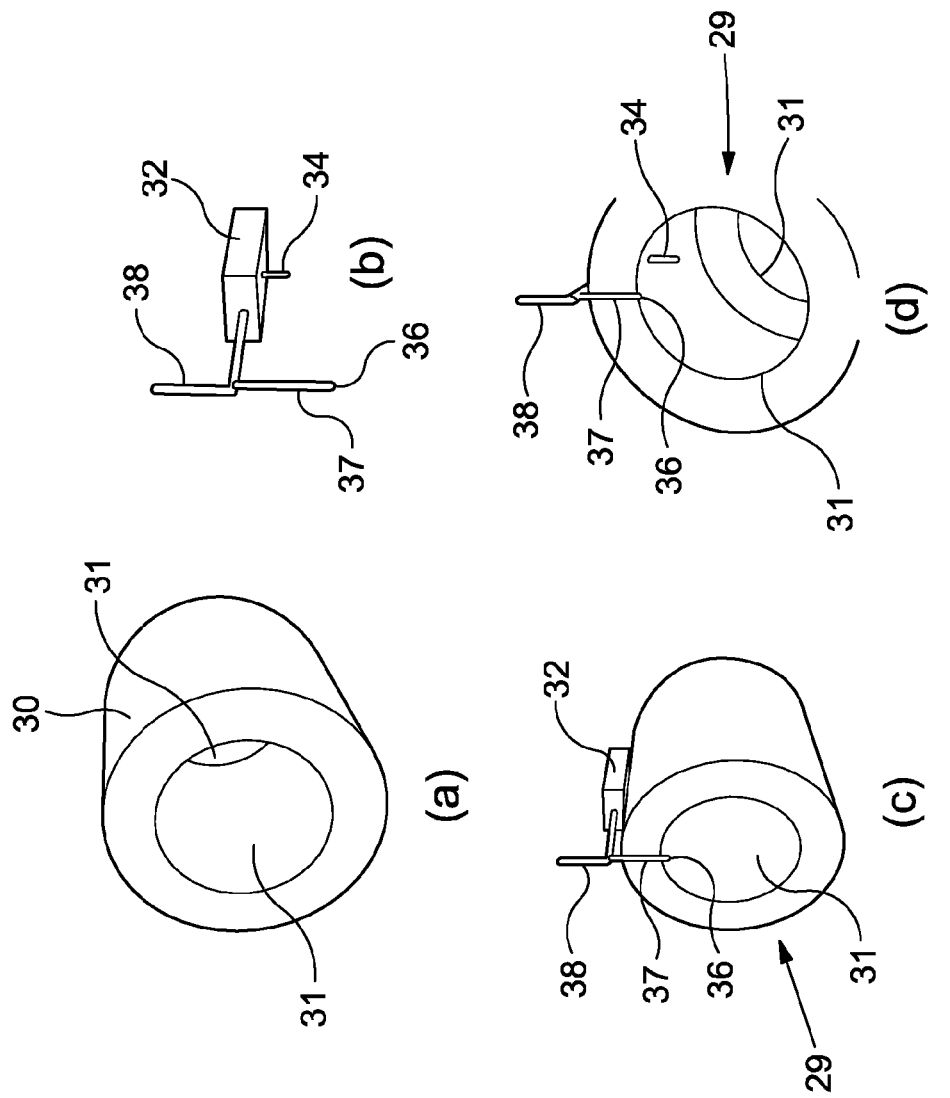
FIG. 4(a) shows a cavity member of the fluid sensor of FIG. 1.
FIG. 4(b) shows an electronics enclosure, an antenna, a temperature sensor and cabling of the fluid sensor of FIG. 1.
FIG. 4(c) shows an electrical assembly comprising the cavity member of FIG. 4(a) and the electronics enclosure, antenna, temperature sensor and cabling of FIG. 4(b)
FIG. 4(d) is an alternative perspective view of the electrical assembly of FIG. 4(c) showing the antenna penetrating into an interior of the cavity member.

The main body portion 14 of the fluid sensor 10 is shown in more detail in FIGS. 2(a) and 2(b). In the interests of clarity, FIGS. 2(a) and 2(b) show the main body portion 14 of the fluid sensor 10 after removal of an external casing and filler material. The main body portion 14 of the fluid sensor 10 comprises a base member in the form of a base pipe 20 which defines a fluid flow path 21 internally thereof. The configuration of the base pipe 20 is selected to withstand a predetermined fluid pressure within the fluid flow path 21 whilst also being substantially transparent to radio-frequency (RF) radiation. In the example of FIGS. 2(a) and 2(b), the base pipe 20 is formed from a composite material comprising E-glass reinforcing elements embedded within a PEEK matrix.

The main body portion 14 of the fluid sensor 10 comprises flanges 22 located at either end thereof. Each flange 22 is configured for connection of the main body portion 14 to a corresponding flange of an adjacent length of pipeline 12. The base pipe 20 extends between the flanges 22. The main body portion 14 of the fluid sensor 10 comprises tie bars 24 which serve to connect the flanges 22 together. The flanges 22 and/or the base pipe 20 are configured such that, in use, the tie bars 24 may be tensioned to compress the base pipe 20 according to the application for which the pipeline 12 is intended, for example according to the environment in which the pipeline 12 is to be deployed. The flanges 22 and/or the tie bars 24 may be formed from a metal such as steel or from a composite material comprising carbon fibre reinforcing elements embedded in a PEEK matrix. The construction of the main body portion 14 of the fluid sensor 10 is described below in more detail with reference to FIG. 3(a)-FIG. 7.

The manufacture of the main body portion 14 of the fluid sensor 10 begins with the provision of the base pipe 20 shown in FIG. 3(a). A cavity filler member generally designated 26 is formed around the base pipe 20 as shown in FIGS. 3(b) to 3(d). The base pipe 20 and the cavity filler member 26 together form a core generally designated 27. The cavity filler member 26 comprises a plurality of PEEK rings 28 which are separately formed and subsequently co-axially arranged along the base pipe 20. Each ring 28 is generally planar and comprises generally parallel faces. A face of each ring 28 engages an opposing face of an adjacent ring 28 to form the cavity filler member 26. Adjacent rings 28 may be bonded together with a thin layer of epoxy resin (not shown) which is substantially transparent to RF radiation.

With reference to FIGS. 4(c) and 4(d), the manufacture of the main body portion 14 of the fluid sensor 10 continues with the formation of an electrical assembly generally designated 29. The electrical assembly 29 comprises a generally cylindrical copper cavity member 30 having apertures 31 formed in either end. The cavity member 30 is shown in isolation in FIG. 4(a). As shown in isolation in FIG. 4(b), the electrical assembly 29 further comprises an electronics enclosure 32, an antenna 34, a temperature sensor in the form of a platinum resistance thermometer 36 and associated cabling 37, and cabling 38 for communication with the electronic instrumentation 16. As shown in FIG. 4(d), the antenna 34 extends through a wall of the cavity member 30 into an interior of the cavity member 30. The antenna 34 is electrically insulated from the cavity member 30. The electronics enclosure 32 provides an enclosure for electronics which are described in more detail below. It should also be understood that the electronics enclosure 32 is attached to the cavity member 30 by an arrangement of fasteners and/or one or more brackets (not shown).

Figure 5:
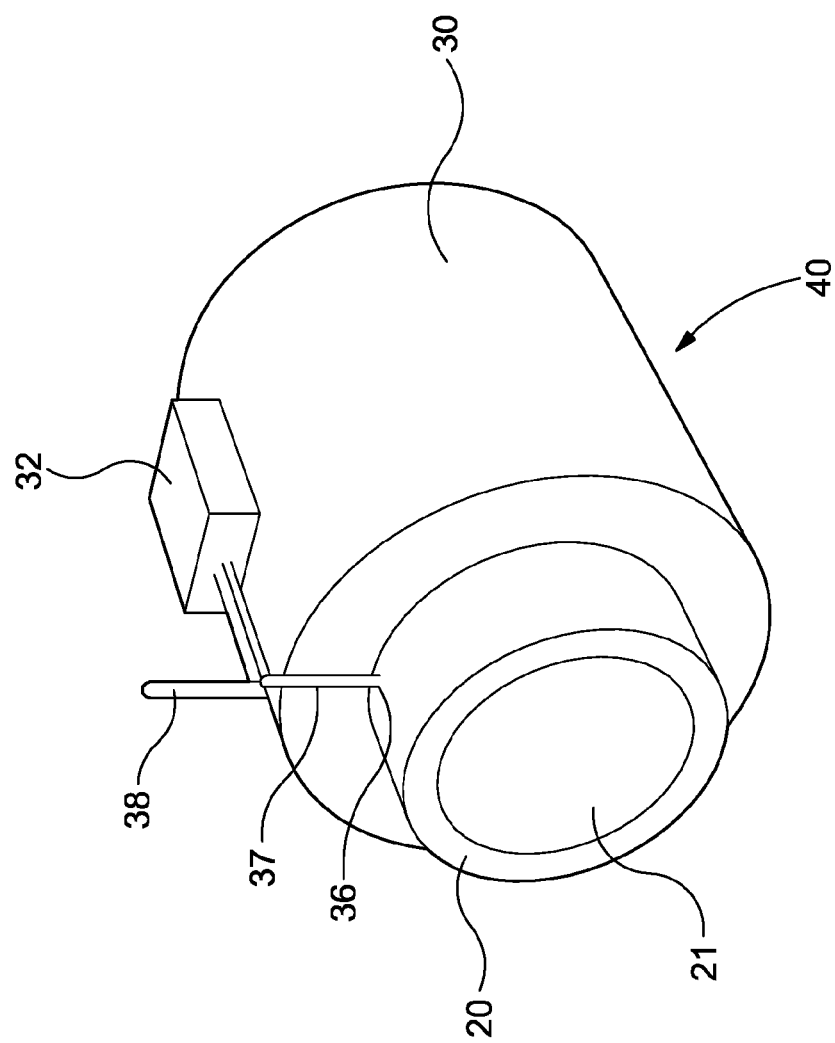
FIG. 5 shows the electrical assembly of FIGS. 4(c) and 4(d) mounted relative to the core of FIGS. 3(b)-3(d)
Figure 6:
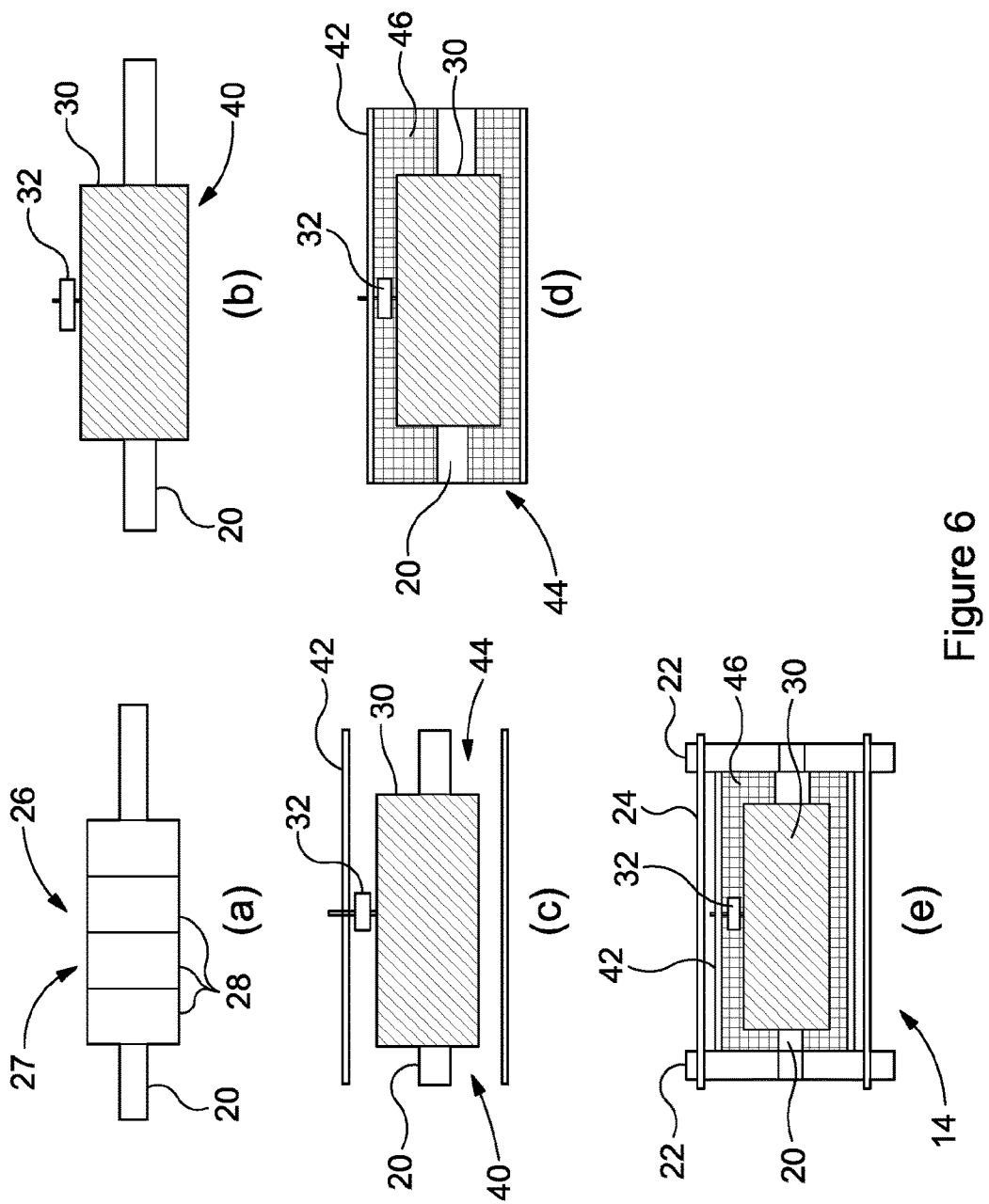
FIG. 6(a)-6(e) illustrate partial axial cross-sections of the main body portion of the fluid sensor of FIG. 1 at various stages during manufacture.

The electrical assembly 29 is fitted over the core 27 to provide the cavity assembly 40 shown in FIG. 5. A summary of the manufacturing steps discussed above with reference to FIGS. 3(a) to FIG. 5 is provided by FIGS. 6(a) and 6(b). The manufacture of the main body portion 14 of the fluid sensor 10 continues as described with reference to FIGS. 6(c) to 6(e). As shown in FIG. 6(c), the cavity assembly 40 is fitted inside an external casing 42 thereby defining an extra-cavity region generally designated 44 externally of the cavity member 30 and internally of the external casing 42. The external casing 42 is configured to withstand external pressures such as external fluid pressures which may depend on the external environment in which the main body portion 14 of the fluid sensor 10 is to be deployed. The external casing 42 is formed from a composite material comprising carbon fibre reinforcing elements embedded in a PEEK matrix. As shown in FIG. 6(d), the extra-cavity region 44 is subsequently filled with a relatively incompressible neoprene filler material 46 to provide structural support for the external casing 42 and to provide the main body portion 14 of the fluid sensor 10 with a degree of resistance to shock and vibration. The manufacture of the main body portion 14 of the fluid sensor 10 is completed by fitting the flanges 22 and the tie bars 24 as shown in FIG. 6(e) and as described in more detail with reference to FIG. 7 below.

Figure 7:
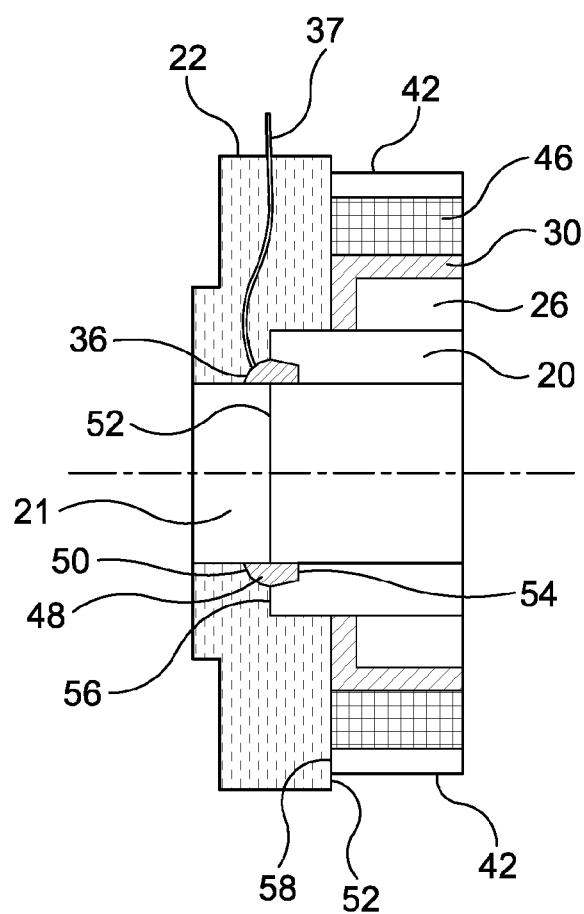
FIG. 7 is an axial cross-section of an end region of the main body portion of the fluid sensor of FIG. 1.

FIG. 7 illustrates an axial cross-section of an end region of the main body portion 14 of the fluid sensor 10 of FIG. 6(e) in more detail. The main body portion 14 of the fluid sensor 10 comprises an inner seal ring 48 accommodated between an annular recess 50 formed in a rear face 52 of the flange 22 and an annular recess 54 formed in an end face 56 of the base pipe 20. The inner seal ring 48 is formed from a composite material comprising carbon fibre reinforcing elements embedded in a PEEK matrix. The inner seal ring 48 is compressed between the rear face 52 of the flange 22 and the end face 56 of the base pipe 20 as the tie bars 24 are tensioned so as to form a fluid tight seal therebetween and thereby prevent fluid from escaping from the fluid flow path 21 along the interface between the rear face 52 of the flange 22 and the end face 56 of the base pipe 20. The inner seal ring 48 is configured so as to accommodate the platinum resistance thermometer 36 and permit location of the platinum resistance thermometer 36 close to the fluid flow path 21 without penetrating the base pipe 20. The inner seal ring 48 and the flange 22 are also configured to accommodate the cabling 37 which connects the platinum resistance thermometer 36 to the electronics enclosure 32. The PEEK matrix/carbon fibre composite inner seal ring 48 is sufficiently thermally conductive to permit the platinum resistance thermometer 36 to accurately measure a temperature of the fluid flowing along the fluid flow path 21. Although not shown in FIG. 7, it should be understood that the main body portion 14 of the fluid sensor 10 further comprises an outer elastomeric seal ring accommodated between the rear face 52 of the flange 22 and an end face 58 of the external casing 42 so as to provide a seal between the flange 22 and the external casing 42 to thereby prevent any ingress of fluid from the external environment into the main body portion 14 of the fluid sensor 10.

Figure 8:
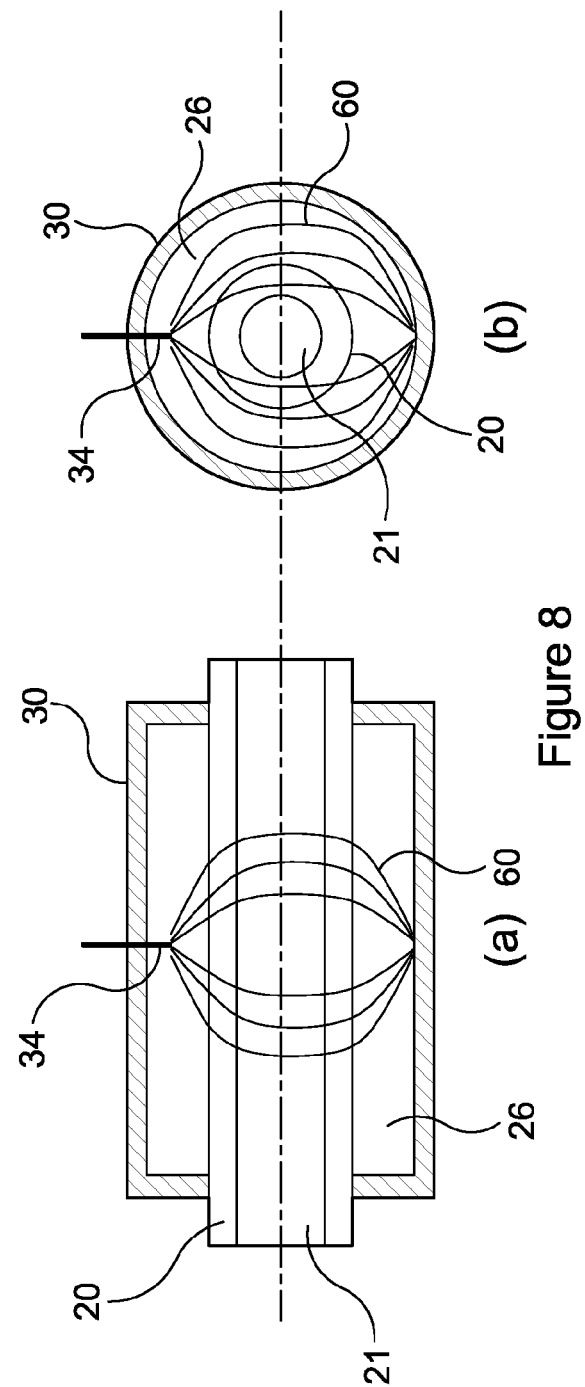
FIG. 8(a) schematically illustrates the axial distribution of an electromagnetic field along the main body portion of the fluid sensor of FIG. 1.
FIG. 8(b) schematically illustrates the distribution of an electromagnetic field across a cross-section of the main body portion of the fluid sensor of FIG. 1.
Figure 9:
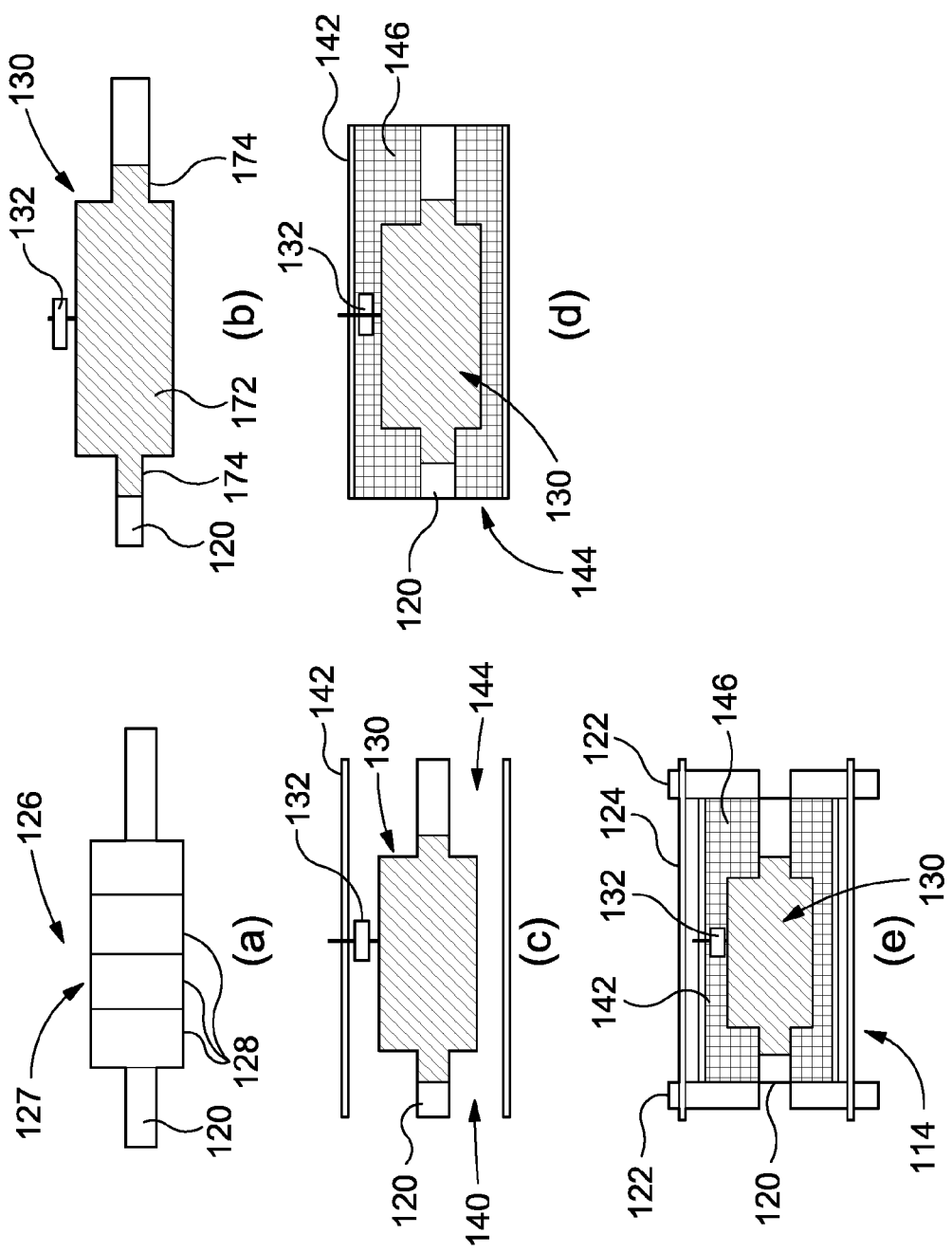
FIG. 9(a)-9(e) illustrate partial axial cross-sections at various stages in the manufacture of a main body portion of an alternative fluid sensor having an alternative cavity member configuration.

The electronics enclosure 32 contains an electromagnetic energy source in the form of an electronic oscillator (not shown) which is configured to oscillate at a predetermined radio frequency at or around a resonant frequency which is dependent on the configuration of the base member 20, the cavity filler member 26, the cavity member 30 and any fluid present in the fluid flow path 21. The oscillator is electrically connected between the cavity member 30 and the antenna 34. In use, electromagnetic energy created by the oscillator circulates between the antenna 34 and the cavity member 30 and is amplified by the oscillator so as to create an RF electromagnetic field 60 which extends between the antenna 34 and the cavity member 30 through the fluid flow path 21 as shown in FIGS. 8(a) and 8(b). It should be understood that the distribution of the electromagnetic field 60 is only schematically represented in FIGS. 8(a) and 8(b) and that the actual distribution of the RF electromagnetic field 60 may differ from that shown in FIGS. 8(a) and 8(b).

The electromagnetic field 60 has a complex frequency spectrum comprising an amplitude spectrum and a phase spectrum each of which may include one or more resonant features each having a frequency, size and/or shape which vary according to the composition, distribution and/or flow characteristics of any fluid in the fluid flow path 21. An output RF signal which is proportional to or representative of a strength of the electromagnetic field 60 is generated within the electronic enclosure 32 and transmitted from the electronic enclosure 32 along the cable 38 to the electronic instrumentation 16. With reference to FIG. 1, the electronic instrumentation 16 comprises a demodulator 62, a processor 64 and a memory 66. As indicated by the dotted line 68, the memory 66 is configured for communication with the processor 64. The demodulator 62 demodulates the output RF signal to form a demodulated signal 70 which is transmitted to the processor 64. The processor 64 analyses the demodulated signal 70 and determines the resonance frequency and the size and shape of the resonance peak from the frequency spectrum of the demodulated signal 70. The processor 64 receives calibration data from the memory 66 which relates a resonance frequency and the size and/or shape of a resonance peak in the frequency spectrum of the demodulated signal 70 to known compositions, distributions and/or known flow rates of fluid in the fluid flow path 21. The processor 64 uses the calibration data and the determined resonance frequency and the determined size and shape of the resonance peak in the frequency spectrum of the demodulated signal 70 to determine the composition, distribution and/or flow rate of the fluid in the fluid flow path 21.

FIGS. 9(a)-9(e) illustrate axial cross-sections at various stages in the manufacture of a main body portion 114 of an alternative fluid sensor. It should be understood that the various stages in the manufacture of the main body portion 114 of the alternative fluid sensor shown in FIGS. 9(a)-9(e) are generally identical to the corresponding stages in a fracture of the main body portion 14 of the fluid sensor shown in FIGS. 6(a)-6(e). As such, the main body portion 114 of the alternative fluid sensor and the main body portion 14 of the fluid sensor 10 have many like features, and like features in FIGS. 9(a)-9(e) share like reference numerals with FIGS. 6(a)-6(e). The only difference between the main body portion 114 of the alternative fluid sensor and the main body portion 14 of the fluid sensor 10 is that the cavity member 130 comprises a generally cylindrical main body portion 172 having an inner diameter which is greater than an outer diameter of the base pipe 120 and generally cylindrical end portions 174, each end portion 174 extending from a different end of the main body portion 172 along the base pipe 120 and each end portion 174 having a reduced inner diameter relative to the inner diameter of the main body portion 172. As shown in FIGS. 9(a) through 9(e), each end portion 174 has an inner diameter which is substantially equal to an outer diameter of the base pipe 120. The cavity member 130 may serve to confine an electromagnetic field across the fluid flow path more effectively than the generally cylindrical cavity member 30. In particular, the cavity member 130 may serve to prevent the electromagnetic field from unduly extending axially along the direction of fluid flow through the apertures at either end of the cavity member 130.

Figure 10:
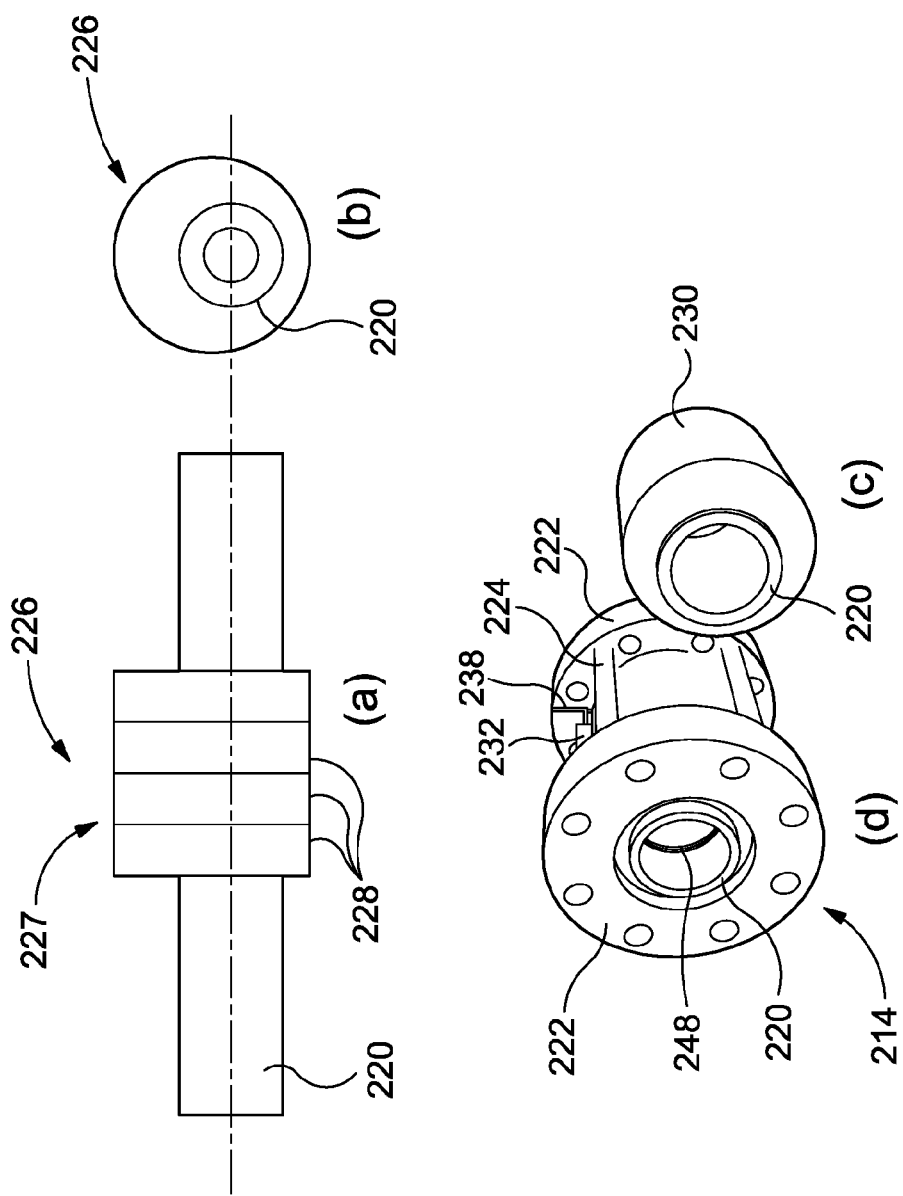
FIG. 10(a) is a side view of an eccentric core comprising a cavity filler member mounted eccentrically on a base pipe.
FIG. 10(b) is an end view of the eccentric core of FIG. 10(a)
FIG. 10(c) is a perspective view of an eccentric cavity member assembly comprising a cavity member mounted on the eccentric core of FIGS. 10(a) and 10(b)
FIG. 10(d) is a perspective view of a main body portion of an eccentric fluid sensor formed from the eccentric cavity member assembly of FIG. 10(c) after removal of an external casing and filler material.

FIG. 10(a)-10(d) illustrate various stages during the manufacture of a main body portion 214 of an eccentric fluid sensor. In the interests of clarity, FIG. 10(d) shows the main body portion 214 of the eccentric fluid sensor after removal of an external casing and filler material. It should be understood that the various stages in the manufacture of the main body portion 214 of the eccentric fluid sensor shown in FIGS. 10(a)-10(d) are generally identical to the corresponding stages in the manufacture of the main body portion 14 of the fluid sensor 10 shown in FIGS. 6(a)-6(e). As such, the main body portion 214 of the eccentric fluid sensor and the main body portion 14 of the fluid sensor 10 have many like features which share like reference numerals. The main difference between the main body portion 214 of the eccentric fluid sensor and the main body portion 14 of the fluid sensor 10 is that the main body portion 214 of the eccentric fluid sensor comprises a cavity filler member 226 mounted eccentrically on a base pipe 220 as shown in FIGS. 10(a) and 10(b). The base pipe 220 and the cavity filler member 226 together form an eccentric core generally designated 227. As shown in FIG. 10(c) an eccentric cavity member 230 is subsequently fitted over the eccentric core 227 of FIGS. 10(a) and 10(b). As for the main body portion 14 of the fluid sensor 10, the manufacture of the main body portion 214 of the eccentric fluid sensor is completed by incorporating an electronics enclosure 232, a temperature sensor (not shown) and cabling 238. Flanges 222 are attached to either end of the base pipe 220, and the inner seal rings 248 and the outer seal rings (not shown) are compressed by tensioning tie bars 224 to arrive at the main body portion 214 shown in FIG. 10(d).

Figure 11:
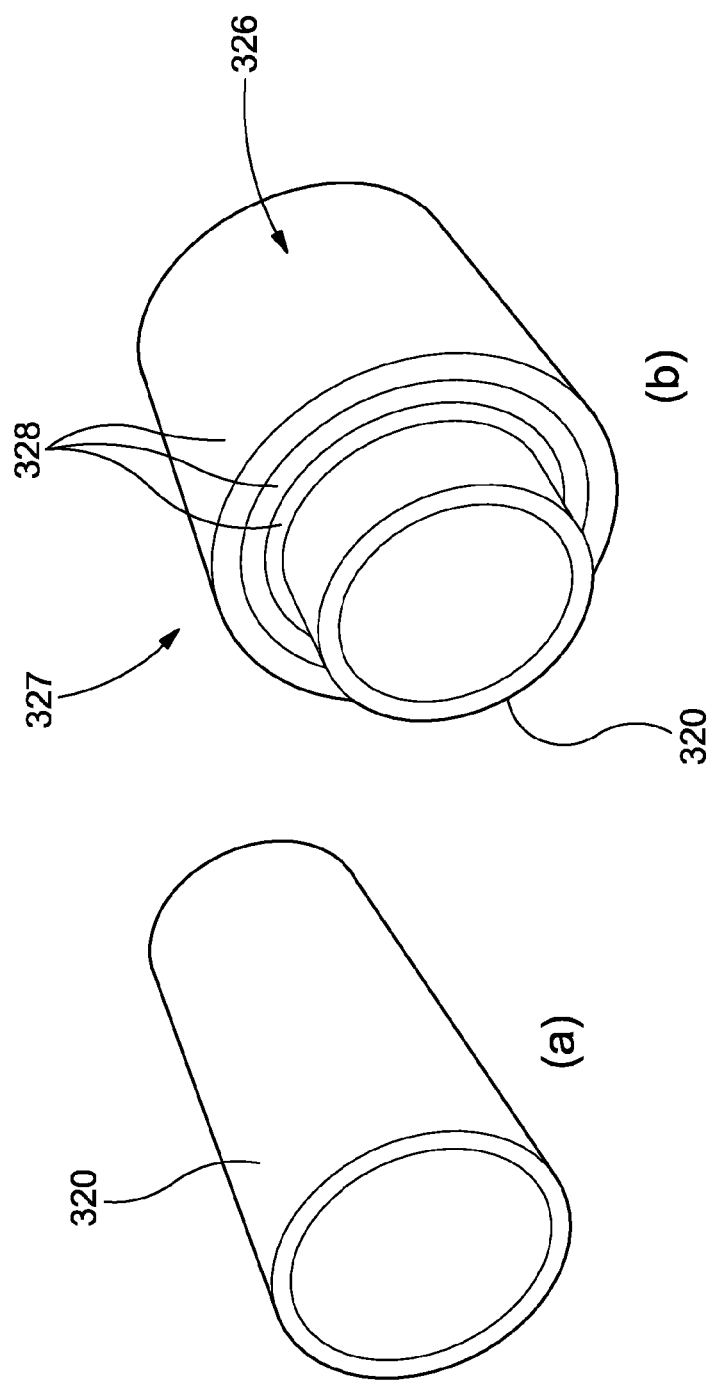
FIG. 11(a) shows a base pipe of a main body portion of an alternative fluid sensor.
FIG. 11(b) shows a core for an alternative fluid sensor comprising a cavity filler member formed from multiple tubular sleeves mounted on the base pipe of FIG. 11(a)

FIG. 11(a) shows a base pipe 320 of a main body portion of an alternative fluid sensor. The base pipe 320 is formed from a composite material comprising E-glass reinforcing elements embedded in a PEEK matrix. FIG. 11(b) shows a corresponding core comprising a cavity filler member generally designated 326 formed from multiple PEEK sleeves 328 mounted on the base pipe 320. The innermost sleeve 328 is cold-fitted over the base pipe 320 and each subsequent tubular sleeve 328 is separately formed and cold-fitted over a preceding tubular sleeve 328. It should be understood that the rest of the manufacturing process of the main body portion of the alternative fluid sensor continues as for the main body portion 14 of the fluid sensor 10.

Figure 12:
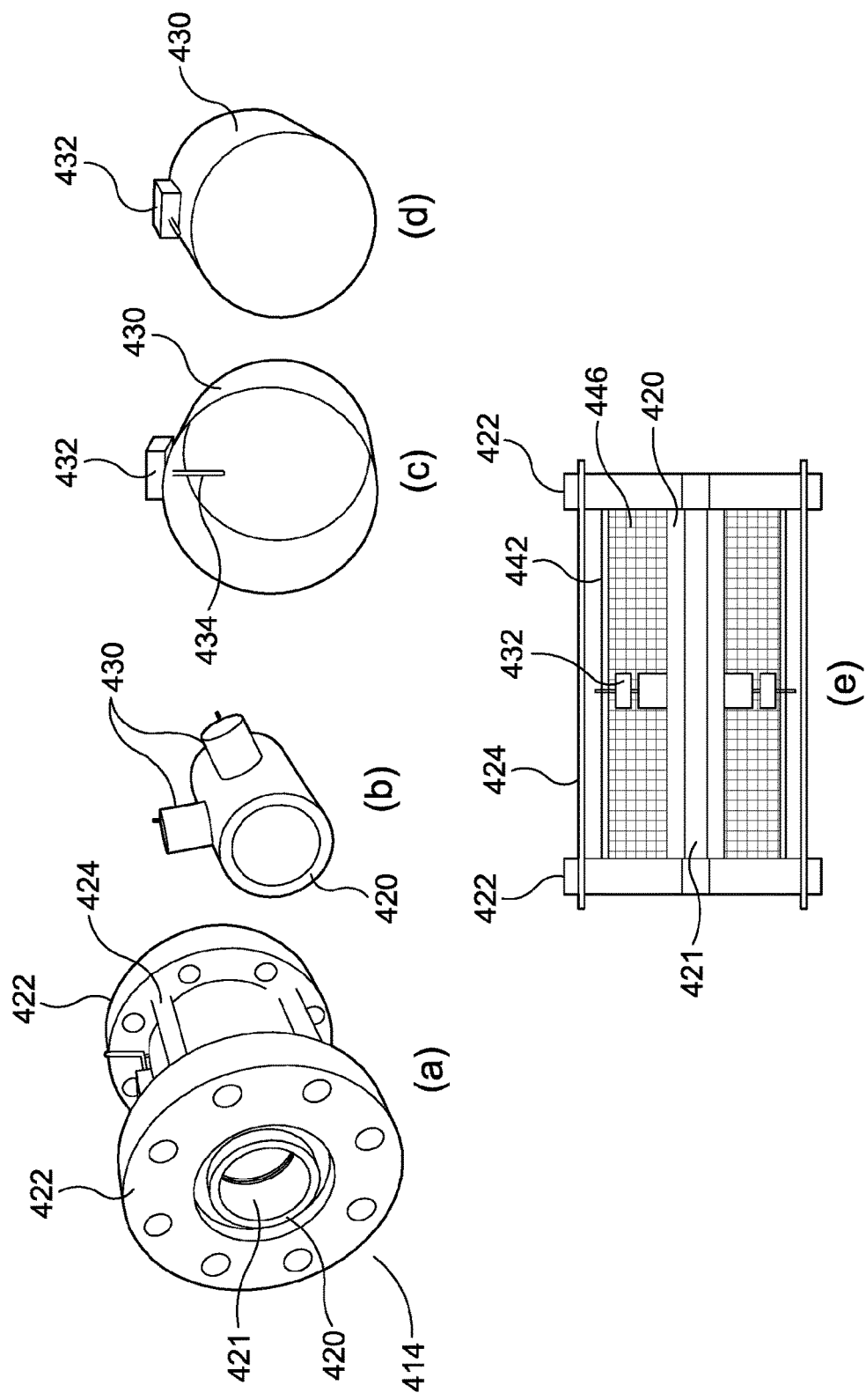
FIG. 12(a) shows a main body portion of a further alternative fluid sensor after removal of an external casing and filler material.
FIG. 12(b) shows a base pipe and two of the radially-arranged cavity members of the main body portion of FIG. 12(a) of the further alternative fluid sensor.
FIG. 12(c) is an electrical assembly for the further alternative fluid sensor including one of the radially-arranged cavity members of FIG. 12(b) viewed from an open end of the cavity member.
FIG. 12(d) is the electrical assembly of FIG. 12(c) viewed from a closed end of the cavity member.
FIG. 12(e) illustrates a partial axial cross-section of the main body portion of FIG. 12(a) of the further alternative fluid sensor.
Figure 13:
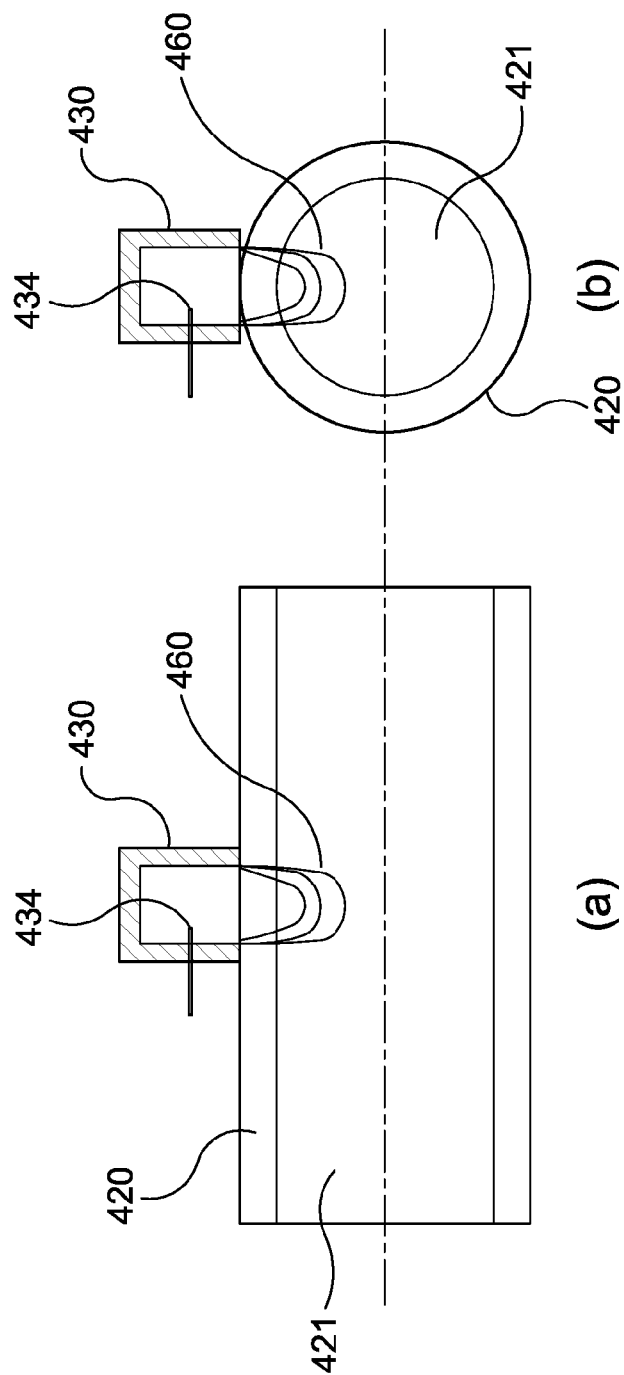
FIG. 13(a) schematically illustrates the axial distribution of an electromagnetic field along the cavity member of the main body portion of FIG. 12(a) of the further alternative fluid sensor.
FIG. 13(b) schematically illustrates the distribution of an electromagnetic across a cross-section of the cavity member of the main body portion of FIG. 12(a) of the further alternative fluid sensor.

FIG. 12(a) shows a main body portion 414 of a further alternative fluid sensor after removal of an external casing and filler material. The main body portion 414 of the further alternative fluid sensor shares many like features with the body portion 14 of the fluid sensor 10 and, as such, like features share like reference numerals. As shown in FIG. 12(b) the main body portion 414 of the further alternative fluid sensor, comprises a PEEK/E-glass base pipe 420 and two radially-arranged cavity members 430. The base pipe 420 defines a fluid flow path 421. As shown in FIGS. 12(c) and 12(d), each cavity member 430 has one open end and one closed-end. The open end of each cavity member 430 is disposed towards the base pipe 420. FIG. 12(e) shows an axial cross-section of the main body portion 414 of FIG. 12(a) of the further alternative fluid sensor including an external casing 442 and neoprene filler material 446. In use, an electromagnetic field 460 extends into the fluid flow path 421 as shown schematically in FIGS. 13(a) and 13(b). It should be understood that the distribution of the electromagnetic field 460 is only schematically represented in FIGS. 13(a) and 13(b) and that the distribution of the RF electromagnetic field 460 may differ from that shown in FIGS. 13(a) and 13(b). The use of one or more radially arranged cavity members 430 may permit the composition and/or flow rate of fluid in one or more different regions of the fluid flow path 421 to be determined.

One skilled in the art will understand that various modifications of the foregoing fluid sensors are possible. For example, the base pipe may comprise a material other than PEEK/E-glass which also permits transmission therethrough of electromagnetic radiation at a frequency of the electromagnetic field. The base pipe may be configured so as to withstand internal fluid pressure. The base pipe may be configured to withstand a predetermined axial tension, a predetermined axial compression and/or a predetermined bending stress. The cavity filler member may comprise a material other than PEEK which also permits transmission therethrough of electromagnetic radiation at a frequency of the electromagnetic field.

The base pipe and/or the cavity filler member may be configured so as to be substantially transparent to electromagnetic radiation at RF frequencies. The base pipe and/or the cavity filler member may comprise a material having a permittivity which is relatively constant over a lifetime of the fluid sensor. This may make simplify and/or enhance the accuracy of the determination of the composition and/or flow characteristics of a fluid over the lifetime of the fluid sensor. The base pipe and/or the cavity filler member may comprise a material having a permittivity which is relatively insensitive to temperature. This may make simplify and/or enhance the accuracy of the determination of the composition and/or flow characteristics of a fluid over a wider range of temperatures. The base pipe and/or the cavity filler member may comprise a material having a permittivity which is relatively insensitive to the permeation of fluids such as air or water into or through the base pipe. This may make simplify and/or enhance the accuracy of the determination of the composition and/or flow characteristics of a fluid even if fluids such as air or water into or through the base pipe migrate through or partially penetrate the base pipe and/or the cavity filler member.

The base pipe and/or the cavity filler member may comprise a material having a permittivity which changes in a predictable quantifiable manner as a function of time over a lifetime of the fluid sensor. The base pipe and/or the cavity filler member may comprise a material having a permittivity which changes in a predictable quantifiable manner as a function of temperature. The base pipe and/or the cavity filler member may comprise a material having a permittivity which changes in a predictable quantifiable manner as a function of the degree of permeation of fluids such as air or water into or through the base pipe.

The base pipe and/or the cavity filler member may comprise a polymer material. The base pipe and/or the cavity filler member may comprise a thermoplastic material. The base pipe and/or the cavity filler member may comprise a thermoset material. The base pipe and/or the cavity filler member may comprise a polyaryl ether ketone, a polyaryl ketone, a polyether ketone (PEK), a polyether ether ketone (PEEK), a polycarbonate and/or the like. The base pipe and/or the cavity filler member may comprise polyvinyl chloride (PVC). The base pipe and/or the cavity filler member may comprise a polyamide. The base pipe and/or the cavity filler member may comprise at least one of polyamide 11 (PA11), polyvinylidene fluoride, or polyvinylidene difluoride (PVDF), polyphenylene sulphide (PPS), polyethylenimines (PEI), polyoxymethylene (POM) or acetal. The base pipe and/or the cavity filler member may comprise a resin such as a setting resin, a polymeric resin, an epoxy resin or the like.

The base pipe and/or the cavity filler member may be formed from a composite material comprising a matrix and one or more reinforcing elements embedded within the matrix. The matrix may be substantially transparent to transmission of electromagnetic radiation at a frequency of the electromagnetic field. The matrix may be substantially electrically non-conductive at a frequency of the electromagnetic field. The matrix may comprise a polymer material. The matrix may comprise a thermoplastic material. The matrix may comprise a thermoset material. The matrix may comprise a polyaryl ether ketone, a polyaryl ketone, a polyether ketone (PEK), a polyether ether ketone (PEEK), a polycarbonate and/or the like. The matrix may comprise polyvinyl chloride (PVC). The matrix may comprise at least one of polyamide 11 (PA11), polyvinylidene fluoride, or polyvinylidene difluoride (PVDF), polyphenylene sulphide (PPS), polyethylenimines (PEI), polyoxymethylene (POM) or acetal. The matrix may comprise a resin such as a setting resin, a polymeric resin, an epoxy resin or the like.

The one or more reinforcing elements may be substantially transparent to transmission of electromagnetic radiation at a frequency of the electromagnetic field. The one or more reinforcing elements may be substantially electrically non-conductive at a frequency of the electromagnetic field. The one or more reinforcing elements may comprise continuous or elongate elements. The one or more reinforcing elements may comprise fibres, strands, filaments, nanotubes or the like. The one or more reinforcing elements may comprise discontinuous elements. The one or more reinforcing elements may comprise polymeric fibres, for example aramid fibres. The one or more reinforcing elements may comprise non-polymeric fibres, for example, glass, basalt fibres and/or the like. The one or more reinforcing elements may comprise E-glass. The matrix and the reinforcing elements may comprise similar or identical materials. For example, the reinforcing elements may comprise the same material as the matrix, albeit in a fibrous, drawn, elongate form or the like.

The cavity filler member may be formed in situ relative to the base member. The cavity filler member may be formed in situ over, on and/or around the base member. The cavity filler member may be formed by a casting, moulding, machining and/or deposition process. The cavity filler member may be integrally or monolithically formed.

The cavity member may comprise a metal other than copper. For example, the cavity member may comprise at least one of brass, gold, silver, aluminium, iron, steel, and the like. The cavity member may comprise an electrically conductive composite material comprising a matrix and one or more reinforcing elements embedded within the matrix. The one or more reinforcing may be electrically-conductive. The matrix may be electrically-conductive.

The matrix may comprise at least one of a polymer material, a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA11), polyvinylidene fluoride, polyvinylidene difluoride (PVDF), polyphenylene sulphide (PPS), polyethylenimines (PEI), polyoxymethylene (POM), acetal, a resin, a setting resin, a polymeric resin, and an epoxy resin.

The one or more reinforcing elements may be substantially opaque to transmission of electromagnetic radiation at a frequency of the electromagnetic field. The one or more reinforcing elements may comprise at least one of continuous or elongate elements, fibres, strands, filaments, nanotubes, discontinuous elements, particles, clusters and pieces. The one or more reinforcing elements may comprise carbon. The one or more reinforcing elements may be metallic. The one or more reinforcing elements may comprise metal fibres, metal particles, metal clusters, metal pieces and/or the like. The cavity member may comprise reinforcing elements comprising at least one of copper, brass, gold, silver, aluminium, iron, steel, and the like.

The cavity member may be formed in situ relative to the cavity filler member. For example, the cavity member may be formed by manipulating, working, bending, wrapping, machining, coating, dipping, depositing or otherwise applying cavity member material over, on and/or around the cavity filler member. The cavity member may be formed in situ relative to the cavity filler member by forming a layer such as a foil or a sheet of material over, on and/or around the cavity filler member.

Rather than comprising a single antenna for coupling electromagnetic energy to and from the electromagnetic field, the fluid sensor may comprise a plurality of antennas. Each antenna may be configured to couple electromagnetic energy to and/or from the electromagnetic field. The fluid sensor may comprise a first antenna for coupling electromagnetic energy to the electromagnetic field and a second antenna for coupling electromagnetic energy from the electromagnetic field.

Rather than comprising an electromagnetic energy source in the form of an oscillator, the fluid sensor may comprise a electromagnetic energy source which is configured to amplify electromagnetic energy which is coupled from the electromagnetic field back through the electromagnetic energy source. Together with the one or more antennas, the cavity member and the electromagnetic field, such an electromagnetic energy source may define a resonant system for the electromagnetic field. Such a fluid sensor may create an electromagnetic field having a complex frequency spectrum comprising an amplitude frequency spectrum and a phase frequency spectrum, wherein each of the amplitude and phase frequency spectra of the complex frequency spectrum are dependent on the configuration of the resonant system and, in particular on the configuration of the core, the configuration of the cavity member and on any fluid present in the fluid flow path.

The electromagnetic energy source may comprise at least one of a gain medium, an amplifier, and a negative resistance.

In a further variant, the fluid sensor may be configured to prevent amplification of electromagnetic energy which is coupled from the electromagnetic field back through the electromagnetic energy source. The frequency of the electromagnetic field created by such a fluid sensor may be independent of the configuration of the core, the configuration of the cavity member and of any fluid present in the fluid flow path. Such a fluid sensor may permit electromagnetic energy to be provided to any fluid present in the fluid flow path. Energy may be provided to a fluid present in the fluid flow path for the purposes of determining at least one of a composition, distribution and/or flow rate of the fluid. Energy may be provided to a fluid present in the fluid flow path for the purposes of heating the fluid, agitating the fluid, exciting the fluid and/or imaging the fluid.

The temperature sensor may comprise a temperature sensor other than a platinum resistance thermometer. For example, the temperature sensor may comprise a resistance temperature detector (RTD) of any kind or a thermocouple, a thermistor, a thermometer or the like.

Rather than being located remotely from the main body portion of the fluid sensor at least one of the demodulator, the processor and the memory may be located adjacent to or incorporated within the main body portion of the fluid sensor.

The invention claimed is:

1. A fluid sensor comprising:
a base member defining a fluid flow path;
a cavity filler member located externally of and circumferentially surrounding the base member; and
a cavity member located externally of and circumferentially surrounding the base member and the cavity filler member,
the cavity member comprises a composite material comprising a matrix and one or more electrically conductive reinforcing elements embedded within the matrix,
the cavity member provides confinement for an electromagnetic field, and the base member and the cavity filler member each permit transmission therethrough of electromagnetic radiation at a frequency of the electromagnetic field,
the electromagnetic field comprises a radio frequency (RF) electromagnetic field,
wherein the base member comprises a composite material comprising a matrix and one or more reinforcing elements embedded within the matrix and the one or more reinforcing elements are substantially electrically non-conductive at a frequency of the electromagnetic field,
the base member and the cavity filler member comprise a polyether ether ketone (PEEK).

2. A fluid sensor according to claim 1, wherein the base member is configured to withstand a predetermined pressure, a predetermined force, a predetermined axial tension, a predetermined axial compression and/or a predetermined bending stress.

3. A fluid sensor according to claim 1, wherein the base member is configured to withstand a predetermined force or pressure exerted on an exterior of the base member and/or a predetermined fluid pressure in the fluid flow path.

4. A fluid sensor according to claim 1, wherein the cavity filler member comprises a composite material comprising a matrix and one or more reinforcing elements embedded within the matrix.

5. A fluid sensor according to claim 4, wherein the one or more reinforcing elements are substantially electrically non-conductive at a frequency of the electromagnetic field.

6. A fluid sensor according to claim 4, wherein the one or more reinforcing elements comprise at least one of polymeric fibres, aramid fibres, non-polymeric fibres, basalt fibres, glass fibres and E-glass fibres.

7. A fluid sensor according to claim 1, wherein the cavity filler member comprises multiple component parts.

8. A fluid sensor according to claim 1, wherein the cavity filler member comprises multiple sleeves.

9. A fluid sensor according to claim 8, wherein the sleeves are generally tubular.

10. A fluid sensor according to claim 8, wherein the sleeves are concentrically arranged.

11. A fluid sensor according to claim 7, wherein the cavity filler member comprises multiple generally flat component parts, each component part has an aperture formed therein through which the base member extends, and the component parts are arranged so that respective faces of adjacent component parts engage one another.

12. A fluid sensor according to claim 11, wherein the aperture is arranged concentrically with respect to an outer circumference of the component part.

13. A fluid sensor according to claim 11, wherein the aperture is arranged eccentrically with respect to an outer circumference of the component part.

14. A fluid sensor according to claim 11, wherein the component part is generally annular.

15. A fluid sensor according to claim 7, wherein the component parts of the cavity filler member are bonded, adhered, fused, welded or joined together.

16. A fluid sensor according to claim 1, wherein the cavity filler member is bonded, adhered, fused, welded or joined to the base member.

17. A fluid sensor according to claim 1, wherein the cavity member comprises an electrically conductive material.

18. A fluid sensor according to claim 1, wherein the cavity member comprises a metal.

19. A fluid sensor according to claim 1, wherein the cavity member comprises at least one of copper, brass, gold, silver, aluminium, iron and steel.

20. A fluid sensor according to claim 1, wherein the matrix comprises at least one of a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA 11), polyvinylidene fluoride, polyvinylidene difluoride (PVDF), polyphenylene sulphide (PPS), polyethylenimines (PEI), polyoxymethylene (POM), acetal, a resin such as a setting resin, a polymeric resin, and an epoxy resin.

21. A fluid sensor according to claim 1, wherein the one or more reinforcing elements comprise carbon fibres.

22. A fluid sensor according to claim 1, wherein the cavity member is generally cylindrical.

23. A fluid sensor according to claim 1, wherein the cavity has an aperture formed therein.

24. A fluid sensor according to claim 1, wherein the cavity member has two opposite ends, each end having an aperture formed therein.

25. A fluid sensor according to claim 1, wherein the cavity member has an open end and a closed end.

26. A fluid sensor according to claim 1, wherein the cavity member is separated from an outer surface of the base member.

27. A fluid sensor according to claim 1, wherein the cavity member is separated from the outer surface of the base member by the cavity filler member.

28. A fluid sensor according to claim 1, wherein the cavity member has an inner diameter greater than an outer diameter of the base member.

29. A fluid sensor according to claim 1, wherein the cavity member comprises a generally tubular main body portion and a generally planar end portion at each end thereof, wherein each of the end portions has an aperture formed therein and a respective face of each of the end portions engages a respective end face of the main body portion.

30. A fluid sensor according to claim 1, wherein the cavity member comprises a generally cylindrical main body portion and generally tubular end portions extending from opposite ends of the main body portion, each end portion having a reduced inner diameter relative to the inner diameter of the main body portion.

31. A fluid sensor according to claim 30, wherein the main body portion has an inner diameter greater than an outer diameter of the base member and each end portion has an inner diameter which is substantially equal to an outer diameter of the base member.

32. A fluid sensor according to claim 1, wherein the cavity member is concentrically aligned with respect to the base member.

33. A fluid sensor according to claim 1, wherein the cavity member is eccentrically aligned with respect to the base member.

34. A fluid sensor according to claim 1, wherein an axis of the cavity member is oriented radially relative to an axis of the base member.

35. A fluid sensor according to claim 1, wherein the cavity member is bonded, adhered, fused, welded or otherwise joined to the base member and/or to the cavity filler member.

36. A fluid sensor according to claim 1, comprising an external casing configured to protect the cavity member.

37. A fluid sensor according to claim 36, wherein an extra-cavity region is defined externally of the cavity member and internally of the external casing.

38. A fluid sensor according to claim 37, comprising a filler material which at least partially fills the extra-cavity region.

39. A fluid sensor according to claim 38, wherein the filler material comprises at least one of a solid potting compound, a gelatinous potting compound, a thermo-setting plastic, silicone rubber, an incompressible material, and neoprene.

40. A method for use in manufacturing a fluid sensor, the method comprising:
   providing a base member defining a fluid flow path;
   locating a cavity filler member externally of and circumferentially surrounding the base member;
   locating a cavity member externally of and circumferentially surrounding the base member and the cavity filler member,
   wherein the cavity member provides confinement for an electromagnetic field, the cavity member comprises a composite material comprising a matrix and one or more electrically conductive reinforcing elements embedded within the matrix, and the base member and the cavity filler member each permit transmission therethrough of electromagnetic radiation at a frequency of the electromagnetic field,
   wherein the base member comprises a composite material comprising a matrix and one or more reinforcing elements embedded within the matrix and the one or more reinforcing elements are substantially electrically nonconductive at a frequency of the electromagnetic field.

* * * * *